United States Patent
Nagano et al.

(10) Patent No.: US 9,040,905 B2
(45) Date of Patent: May 26, 2015

(54) ANALYSIS DEVICE AND ANALYSIS METHOD

(75) Inventors: Hisashi Nagano, Nishitokyo (JP); Yasutaka Suzuki, Kodaira (JP); Hideo Kashima, Kokubunji (JP); Yuichiro Hashimoto, Tachikawa (JP); Masuyuki Sugiyama, Hino (JP); Masakazu Sugaya, Inagi (JP); Yasunori Doi, Hitachi (JP); Koichi Terada, Kamakura (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 13/884,755

(22) PCT Filed: Nov. 8, 2011

(86) PCT No.: PCT/JP2011/075666
§ 371 (c)(1),
(2), (4) Date: Jun. 27, 2013

(87) PCT Pub. No.: WO2012/063796
PCT Pub. Date: May 18, 2012

(65) Prior Publication Data
US 2014/0151543 A1     Jun. 5, 2014

(30) Foreign Application Priority Data

Nov. 11, 2010  (JP) ................................ 2010-252663
Aug. 23, 2011  (JP) ................................ 2011-181058
Aug. 23, 2011  (JP) ................................ 2011-181090

(51) Int. Cl.
*H01J 49/04*     (2006.01)
*G01N 1/22*      (2006.01)
(Continued)

(52) U.S. Cl.
CPC ............. *H01J 49/04* (2013.01); *H01J 49/0468* (2013.01); *G01N 1/2211* (2013.01);
(Continued)

(58) Field of Classification Search
CPC ... H01J 49/04; H01J 49/0459; H01J 49/0468; H01J 49/049; G01N 1/02; G01N 1/04; G01N 1/2211; G01N 1/24
USPC .......................................................... 250/288
See application file for complete search history.

(56) References Cited

U.S. PATENT DOCUMENTS 5,162,652 A * 11/1992 Cohen et al. ................... 250/288
5,345,809 A     9/1994 Corrigan et al.
(Continued)

FOREIGN PATENT DOCUMENTS

CN          1836621          9/2006
EP      000447158 A2  *  9/1991
(Continued)

OTHER PUBLICATIONS

International Search Report for International Application No. PCT/JP2011/075666, Dec. 27, 2011.
(Continued)

*Primary Examiner* — Jack Berman
(74) *Attorney, Agent, or Firm* — Baker Botts L.L.P.

(57) ABSTRACT

Provided is a technique of analyzing particles in real time while collecting and condensing the particles continuously. Gas and/or particles as a detection target substance that are attached to an authentication target 2 are removed by air flow from a blowing region 5. The removed sample is sucked and is condensed and sampled at a sampling region 10, and ions of the sample are generated at an ion source 21 and are then subjected to mass analysis at a mass analysis region 23. Determination of the obtained mass spectrum is made as to the presence or not of a mass spectrum derived from the detection target substance, and a monitor 27 displays a result thereof. Thereby, the detection target substance attached to the authentication target 2 can be detected continuously in real time, promptly and with a less error rate.

20 Claims, 30 Drawing Sheets

(51) Int. Cl.
  *G01N 1/02*  (2006.01)
  *H01J 49/00*  (2006.01)
  *G01N 33/00*  (2006.01)

(52) U.S. Cl.
  CPC ....... *G01N 1/2214* (2013.01); *G01N 2001/028* (2013.01); *H01J 49/00* (2013.01); *H01J 49/0036* (2013.01); *H01J 49/0459* (2013.01); *G01N 33/0057* (2013.01)

(56) References Cited

U.S. PATENT DOCUMENTS

| | | | |
|---|---|---|---|
| 6,746,500 | B1 | 6/2004 | Park et al. |
| 7,141,786 | B2 * | 11/2006 | McGann et al. ............... 250/287 |
| 8,101,001 | B2 * | 1/2012 | Qian ............................... 55/441 |
| 2002/0024442 | A1 * | 2/2002 | Nishikawa et al. ........ 340/573.1 |
| 2003/0193019 | A1 | 10/2003 | Nagano et al. |
| 2004/0016310 | A1 | 1/2004 | Sakairi et al. |
| 2005/0058575 | A1 | 3/2005 | Ishikawa et al. |
| 2005/0061964 | A1 | 3/2005 | Nagano et al. |
| 2009/0200458 | A1 * | 8/2009 | Kashima et al. .............. 250/282 |
| 2014/0117223 | A1 * | 5/2014 | Stott et al. ..................... 250/282 |

FOREIGN PATENT DOCUMENTS

| | | |
|---|---|---|
| JP | H 3-87629 | 4/1991 |
| JP | H 7-6729 | 1/1995 |
| JP | 2000-28579 | 1/2000 |
| JP | 2000-035383 | 2/2000 |
| JP | 2002-70383 | 3/2002 |
| JP | 2003-524522 | 8/2003 |
| JP | 2003-307507 | 10/2003 |
| JP | 2004-125576 | 4/2004 |
| JP | 2005-91118 | 4/2005 |
| JP | 2005-98706 | 4/2005 |
| JP | 2007-170985 | 7/2007 |
| JP | 2009-031227 | 2/2009 |
| WO | WO 9714033 A1 * | 4/1997 |
| WO | WO 2006/097990 | 9/2006 |
| WO | WO 2007/041947 | 4/2007 |

OTHER PUBLICATIONS

Yasuaki Takada, "Walkthrough-gata Bakuhatsubutsu Tanchi System", Safety Engineering, vol. 35, No. 2, Jun. 1, 2008, pp. 4 to 8, with English translation.

* cited by examiner

Fig. 3

| | Detection target substance component | Positive/ Negative ion | m/z of ion (MS,MSMS) | m/z range | Threshold (Counts) | BG threshold (Counts) | Relation with other component ion | Relation with other foreign substance ion |
|---|---|---|---|---|---|---|---|---|
| 1 | A | Positive | mA1(MS) | ±0.5 | $1 \times 10^7$ | $5 \times 10^6$ | OR with 2 | NOT with M |
| 2 | A | Positive | mA2(MS) | ±0.5 | $2 \times 10^8$ | $1 \times 10^8$ | OR with 1 | |
| 3 | B | Positive | mB1(MS) | ±0.3 | $2 \times 10^6$ | $1 \times 10^6$ | AND with 4, 5 | |
| 4 | B | Negative | mB2(MS) | ±0.5 | $5 \times 10^6$ | $1 \times 10^6$ | AND with 3, 5 | NOT with M |
| 5 | B | Negative | mB3(MSMS) | ±0.3 | $3 \times 10^6$ | $1 \times 10^6$ | AND with 3, 4 | |
| 6 | C | Negative | mC1(MSMS) | ±0.5 | $1 \times 10^7$ | $5 \times 10^6$ | | |
| ⋮ | ⋮ | ⋮ | ⋮ | ⋮ | ⋮ | ⋮ | ⋮ | ⋮ |
| M | Foreign substance component A | Negative | mKA1(MS) | ±0.5 | $1 \times 10^7$ | $5 \times 10^6$ | | |

ANALYSIS DEVICE AND ANALYSIS METHOD

TECHNICAL FIELD

The present invention relates to analyzers configured to collect particles for analysis and analysis methods.

BACKGROUND ART

It has been required to analysis particles in gas in the fields of engineering and environment. Known methods to collect particles include cyclonic dust-collecting devices. Patent Literature 1, for example, discloses a method of collecting suspending dust in a clean room using a cyclone and measuring the number of dust particles with a counter.

Patent Literature 2 discloses a method of collecting suspending particles in the air to let the particles adhere to a tape filter, and measuring the weight thereof. Patent Literature 3 discloses a method of sampling sampled particles by an inertial impactor and heating the sampling region to let the particles evaporate for analysis with a mass spectrometer.

Recently the threat of terrorism has increased worldwide, and since a method of producing explosives using daily goods has been widely known, terrorism and crimes using explosives are becoming a threat in daily life as well. In London, simultaneous terrorist acts were committed at subways and buses, resulting in many deaths and injuries. According to the news release, a suspect attempting a suicide attack in a commuter train was arrested in Japan as well.

In order to prevent such terrorism and crimes, techniques to detect dangerous substances have been developed in various countries. Patent Literature 4, for example, describes an explosive detection system using a mass spectrometer. Explosive vapor leaking from luggage is sampled by a sampling probe, which is then ionized by negative corona discharge. The resultant is subjected to detection by a mass spectrometer, thereby determining the presence or not of dangerous substances.

Patent Literature 5 discloses a method of collecting explosive particles to a disk or tape filter using a cyclone, and moving the same to another position to heat the collected explosive particles for evaporation, thus analyzing the resultant by an ion mobility analyzer. Patent Literature 6 describes a portal explosive detector. Air is blown to a subject in a booth-like room from the left and the right, the room having upper and lower walls and left and right walls. This air lets explosive particles attached to the subject fly upward. Then, the explosive particles are sucked through an inlet at the ceiling by a large intake pump and are adsorbed to a filter provided at a rotator. Then, this rotator is rotated, thus moving the filter to an analyzer, where the adsorbed explosive particles are heated for evaporation, thus analyzing the resultant by an ion mobility analyzer.

CITATION LIST

Patent Literatures

Patent Literature 1: JP 2000-35383 A
Patent Literature 2: JP 2009-31227 A
Patent Literature 3: JP 2005-91118 A
Patent Literature 4: JP 2000-28579 A
Patent Literature 5: JPH 7-6729 A (1995)
Patent Literature 6: JPH 3-87629 A (1991)

SUMMARY OF INVENTION

Technical Problem

The technique described in Patent Literature 1 cannot identify the components of the suspending dust. The technique described in Patent Literature 2 also cannot identify the components of the suspending particles. Further, long-duration operation requires a long tape because the tape has to be moved always. The technique described in Patent Literature 3 requires the step of adsorption and heating of the sampling region, thus failing to perform continuous mass-analysis of the particle components. For continuous measurement, the document describes another method of using two inertial impactors alternately, which, however, requires space for the two inertial impactors, thus leading to difficulty in downsizing. In the configuration including valves, particles will be adsorbed to the inside of the valves, requiring cleaning of the valves, and so long operation requires lengthy maintenance.

The technique described in Patent Literature 4 requires the operation of sampling explosive vapor leaking from luggage by a sampling probe. For destructive explosives or propelling charge for military use and industrial explosives used in construction sites, stable substances are used for safety operation, and so they often have relatively lower vapor pressure. This means that, instead of sampling vapor, particles have to be captured for analysis. The technique described in Patent Literature 5 requires the step of adsorption and heating, thus failing to perform continuous real-time analysis.

The technique described in Patent Literature 6 requires the step of adsorption and heating, thus failing to perform continuous real-time analysis. Since the large intake pump sucks the explosive particles via the inlet, such a pump will suck not only the explosive particles but also dust and the like, and cause a clogged filter, thus leading to difficulty in long-duration operation. The large-capacity intake may cause another problem of attenuating the vapor generated from explosive particles.

Conventional explosive detectors like Patent Literature 6 mainly assume the operation at airports or important facilities, and are designed to inspect a relatively small number of persons. For the usage at mass transport systems such as at stations used by many passengers, two factors are important, including high throughput enabling inspection in a short time and a low error rate to reduce an erroneous reaction by a detector to a passenger without carrying explosives. Especially the error reaction requires an inspector to perform careful inspection of baggage, thus adversely affecting the throughput. In this way, the erroneous reaction by the detector leads to difficulty in prompt inspection.

For those reasons, a method of analyzing particles in real time while continuously collecting and condensing the particles has been required. For the usage of inspection for dangerous substances such as explosives and illegal drugs, a method for prompt inspection with a low error rate is required. The method with less maintenance frequency and enabling long-duration operation also is required.

Solution to Problem

It is an object of the present invention to provide an analyzer configured to analyze particles in real time while continuously collecting and condensing the particles. Particles are collected by a cyclonic effect, whereby particles of a particular size can be sampled by a sampling region. The sampled particles are then evaporated by heating the sampling region. Vapor therefrom is sucked from the rear face of the sampling region, is ionized and then is analyzed by a high-sensitive and high-selective mass spectrometer, whereby components of the particles can be identified. Especially, particles subjected to condensation by a cyclonic effect are sampled at the sampling region, and large intake to collect particles and intake for analysis that is to be conveyed to a mass spectrometer are separated at the sampling region, thus reducing the attenuating effect due to the large intake.

An exemplary analyzer of the present invention includes: an authentication region including a face, to which an authentication target is to be brought closer; a blowing region configured to send air flow along the authentication region, thus removing a sample attached to the authentication target; an introduction region configured to suck the sample removed from the authentication target; a sampling region configured to condense and sample the sucked sample; an ion source configured to introduce the sample from the sampling region for ionization; a mass analysis region configured to perform mass analysis of ions generated at the ion source; a data processor configured to control the ion source and the mass analysis region; a database unit configured to hold mass spectrum data derived from a detection target substance; and an identification region configured to compare a result of mass analysis of the sample at the mass analysis region with the mass spectrum data held at the data base unit, thus determining presence or not of the detection target substance.

Advantageous Effects of Invention

The present invention enables analysis of particles in real time while continuously collecting and condensing the particles.

Problems, configurations, and effects other than those explained above will be made apparent by the following explanation of embodiments.

BRIEF DESCRIPTION OF DRAWINGS

FIG. 3 explains an exemplary mass database.

DESCRIPTION OF EMBODIMENTS

Embodiments of the present invention are more specifically described with reference to the drawings. The following device configurations and the process operations are one specific example of the present invention, and the scope of the present invention covers modification examples including the combination or replacement of these embodiments with known techniques.

(A) First Embodiment

Figure 1:
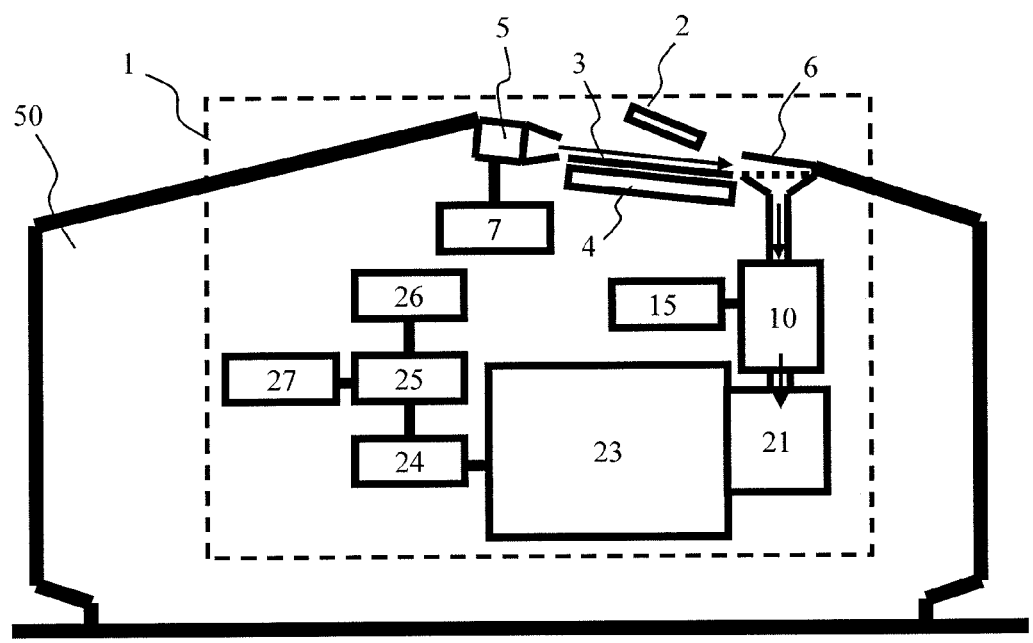
FIG. 1 schematically shows an exemplary analyzer according to the present invention.

The following describes first embodiment of the present invention. FIG. 1 schematically shows an exemplary analyzer according to the present invention, showing an example built in an automatic ticket gate 50 at stations or the like. Other than the automatic ticket gate at stations or the like, this analyzer may be built in a security gate installed at an entrance of facility, a boarding gate at airports or for ships, gates at baggage inspection sites or checked baggage sites, entrance and exit thicket gates at amusement facilities or the like.

An analyzer 1 includes an authentication region 4 having an authentication plane 3, to which an authentication target 2 is to be brought closer for authentication. The authentication target 2 may be an IC card, a mobile phone, a thicket, or a biological part such as a hand, a finger or an eye, for example. A blowing region 5 is provided to send an air flow along the authentication plane 3, thus removing gas and/or particles as a detection target substance attached to the authentication target 2. A blowing control unit 7 is provided so as to control the flow amount or the flow rate, the injection pressure, the temperature, the injection duration, the injection timing and the like of the blowing region 5.

The removed gas and/or particles as the detection target substance are sucked by an introduction region 6. The sucked particles as the detection target substance are condensed for sampling by a sampling region 10. The sampling region 10 is configured to efficiently collect the particles as the detection target substance using a cyclone effect. The sampling region 10 is capable of collecting particles as the detection target substance of a specific size only among the large amount of particles sucked by the introduction region 6, which prevents the sample as the detection target substance from being attenuated by the air flow of suction. A collection filter control unit 15 is provided so as to control the flow amount or the flow rate of suction by the sampling region 10 and the temperature and the operation sequence thereof, for example.

The detection target substance sampled by the sampling region 10 is ionized by an ion source 21. The ionized ions are subjected to mass analysis by a mass analysis region 23. A data processor 24 is provided to control the temperature, the voltage and the operation sequence of the ion source 21 and the mass analysis region 23, thus acquiring mass spectrum data. A mass database region 26 holds mass spectrum data derived from the detection target substance, and an identification region 25 compares the mass analysis result of the sample by the mass analysis region 23 with the mass spectrum data held by the mass database region 26, thus determining the presence or not of the detection target substance. A monitor 27 displays the presence or not of the identified detected target substance and/or the result of analysis. On the basis of the result on the monitor 27, operations are performed, such as displaying of an alarm or the like at the automatic ticket gate 50, closing of the gate of the automatic ticket gate 50, displaying to a monitoring center, recording by a monitoring camera and recording of authentication data.

Figure 2:
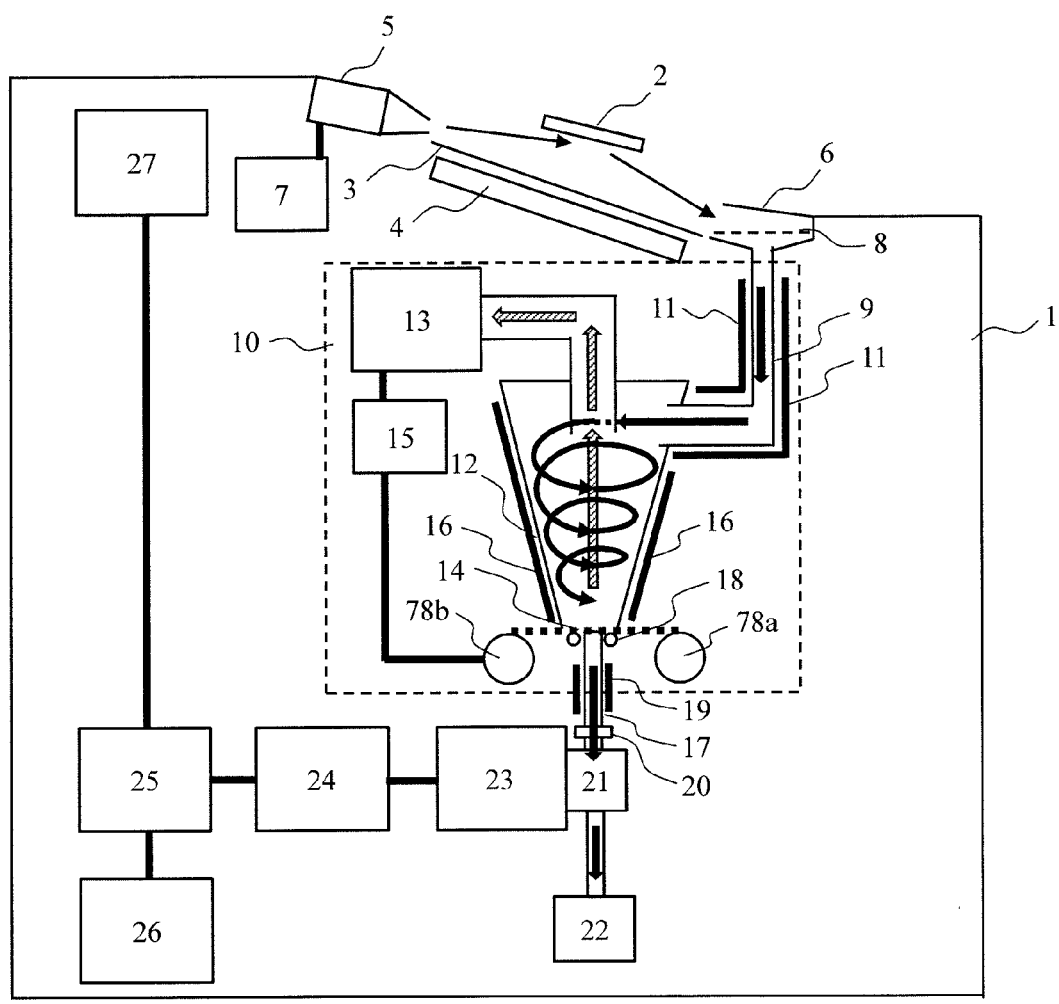
FIG. 2 shows an exemplary internal configuration of an analyzer according to the present invention.

FIG. 2 shows an exemplary internal configuration of an analyzer according to the present embodiment. The analyzer 1 includes the authentication region 4 having the authentication plane 3 to authenticate the authentication target 2, and so includes authentication acquisition means. The authentication plane 3 may be disposed horizontally or diagonally. The authentication plane 3 may be transparent or in a mesh form, and may have a shape letting not only electric waves but also light and air flow from the authentication region 4 pass therethrough. Authentication data obtained by authenticating the authentication target 2 is compared with authentication database provided externally or internally for determination.

The blowing region 5 and the introduction region 6 are disposed so as to sandwich the authentication plane 3 therebetween. The blowing region 5 feeds air flow so as to be along the authentication plane 3, so that when the authentication target 2 approaches the authentication plane 3, the authentication target 2 comes in contact with the air flow fed, thus generating sample gas due to the gas and/or particles as the detection target substance attached to the authentication target 2 or removing the gas and/or particles as the detection target substance. The wind generated from the blowing region 5 so as to remove the gas and/or particles as the detection target substance may be continuous, intermittent, irregular or sporadic. In this way, the gas and/or particles as the detection target substance removed from the authentication target 2 are transferred to the introduction region 6. This air flow is to make sure that the gas and the particles are sucked and detected without being affected by turbulent flow. The air flow is preferably fed in parallel with the authentication plane 3. That is, in order to avoid turbulent flow, the air flow is preferably fed so as not to collide with the authentication plane 3.

The blowing region 5 is connected to the blowing control unit 7 to control the blowing region 5. The blowing control unit 7 controls the flow amount or the flow rate, the injection pressure, the temperature, the injection duration, the injection timing and the like to drive the blowing region 5. The blowing region 5 may always feed air flow, may be driven in synchronization with authentication or may be driven in response to reaction of an external sensor such as a sensor to detect the approaching of a person, a hand or a finger or a sensor to detect the passage of a person. In one example, after receiving an authentication start signal, the blowing region 5 injects air flow at 0.05 MPa of injection pressure having the average flow rate of 49 meter/sec., at the authentication plane 3 for 0.1 sec. of the injection duration, followed by break duration of 0.5 sec. which are alternately performed 10 times continuously.

The transferred gas and/or particles as the detection target substance are sucked from the introduction region 6. The introduction region 6 is provided with a rough mesh filter 8, thus preventing large dust or a finger from entering the introduction region 6. The rough mesh filter 8 used may be a wire net mesh (opening: 0.5 mm, aperture ratio: 50%) as one example. This rough mesh filter 8 is exchangeable, and when the filter is clogged, the filter may be cleaned for reuse or may be exchanged with a new one.

The gas and/or particles as the detection target substance sucked from the introduction region 6 are introduced to the sampling region 10 via an introduction pipe 9. The introduction pipe 9 is heated by a pipe heater 11, thus preventing adsorption of the gas and the particles to the inside of the pipe. In one example, the pipe heater 11 is heated at 120° C. The introduction pipe 9 and the pipe heater 11 may be made as short as possible, or they may be omitted so that the sampling region 10 and the introduction region 6 are directly connected. The sampling region 10 includes a conic condensation device 12, a large intake pump 13, a collection filter 14, a collection filter control unit 15 and an anti adsorption 16. The large intake pump 13 sucks at the flow rate of 40 meter/min., for example. This suction generates a cyclonic effect inside the conic condensation device 12, so that particles of 5 μm or more in size are sampled by the collection filter 14 provided at a small-radius part of the condensation device 12, and other air flow is discharged by the large intake pump 13. The flow amount or the flow rate of the large intake pump 13 can be controlled by the collection filter control unit 15. The large intake pump 13 may always operate, or may operate in synchronization with the operation of the blowing region 5. Alternatively the large intake pump 13 may stop usually or may be controlled so as to operate when the suction amount is small. The anti adsorption 16 may be heated by a heater or may vibrate so as to prevent particles from being adsorbed to the inside of the condensation device 12. The vibration may be given by an ultrasonic transducer, an eccentric rotating motor, a vibrating motor or the like.

Explosive particles typically have a size of 5 μm or more and 100 μm or less, and so particles in this range of size may be collected. The introduction region 6, the introduction pipe 9, the conic condensation device 12 and the like may have their internal faces made of Teflon or may be coated with Teflon, for example. Particles of trimethylenetrinitramine (RDX) or trinitrotoluene (TNT) as main components of plastic explosives charges negatively. Since Teflon also charges negatively, the explosive particles charging negatively have a feature of repelling and hardly being adsorbed.

The collection filter 14 is wound around a filter winding region 78*b* and a filter sending region 78*a*. The filter winding region 78*b* (or the filter sending region 78*a* as well) is controlled by the collection filter control unit 15. Although the collection filter 14 is heated by a collection filter heater 18, not only the particles that are the components as the detection target but also particles as foreign substance components are attached to the collection filter 14, and so the collection filter 14 gets dirty over time. The mass analysis region 23 always and continuously measures a mass spectrum in real time, and so can detect a change of the dirt over time. A value of a background threshold (BG threshold) is used as a threshold of this dirt, and when the dirt exceeds this value, the collection filter 14 is wound up once under the control of the collection filter control unit 15 so that a clean face is exposed. The collection filter 14 used is a ribbon-type filter having the filtering accuracy of 50 μm, the width of 10 mm and the thickness of 0.5 mm. Other than the ribbon type, a plate-type, a rope-like strand, a disk-type or a loop-type filter may be used. When the detection target substance is detected as well, the collection filter 14 may be wound up so that a clean face is exposed, whereby the next measurement can be performed promptly. The collection filter 14 may be made of stainless steel wire, metal fiber, heat-resistance fiber (e.g., cornex), glass fiber or the like.

The collection filter 14 has a rear face (the opposite side of the condensation device 12), to which an analysis pipe 17 is connected. The particles adsorbed to the collection filter 14 are heated by the collection filter heater 18. In one example, it is heated at 230° C. The heated particles are evaporated, and the sample in a gaseous form is then introduced to the ion source 21 via the analysis pipe 17 by an intake pump 22. For example, the intake pump 22 sucks at the flow rate of 2.0 liter/min. The analysis pipe 17 is heated by an analysis pipe heater 19, thus preventing adsorption of gas to the inside of the pipe. For instance, the analysis pipe heater 19 is heated at 120° C. The analysis pipe 17 and the analysis pipe heater 19 may be made as short as possible, or they may be omitted so that the collection filter 14 and the ion source 21 are directly connected. The analysis pipe 17 is provided with a fine mesh filter 20, thus preventing the ion source 21 from getting dirty due to particles that are not gasified at the collection filter 14. The fine mesh filter 20 used may be a stainless steel wire filer or a sintered body filter having filtering accuracy of 50 μm, for example. The fine mesh filter 20 may be cleaned for reuse or may be replaced with a new one if needed.

The ion source 21 used may be an atmospheric pressure chemical ionization source using negative corona discharge or positive corona discharge described in JP 2000-28579 A, for example. Ions may be generated by methods such as radiation from a radiation source, irradiation with electrons, light or laser light, penning discharge, glow discharge, barrier discharge and electrospray.

Ions generated from the sample at the ion source 21 are subjected to mass analysis at the mass analysis region 23. The mass analysis region 23 used may be a wire-type linear ion trap mass spectrometer, for example. The mass analysis may be performed by methods such as a linear ion trap mass spectrometer, a quadruple ion trap mass spectrometer, a quadruple filter mass spectrometer, a triple quadruple mass spectrometer, a time-of-flight mass spectrometer, a magnetic sector-type mass spectrometer, and ion mobility.

A signal obtained at the mass analysis region 23 is measured by the data processor 24 as a mass spectrum. Then, the peaks of mass numbers of the sample are extracted from this mass spectrum. The mass database region 26 holds information containing reference mass analysis data necessary to identify the sample. The information held includes a value of mass-to-charge ratio (m/z) that is the value obtained by dividing the mass number m of ions by the valence z of the ions as well as a relative intensity. The mass spectrum measured at the mass analysis region 23 is sent to the identification region 25, for which data processing such as comparison with data read from the mass database region 26 is performed, thus identifying the sample.

FIG. 3 explains exemplary information held at the mass database region 26. The mass database region 26 stores information such as the component of a sample as a detection target substance, types of positive ion detection or negative ion detection, types of mass spectrometry (MS) or tandem mass spectrometry (MSMS), mass-to-charge ratios of ions derived from the sample as the detection target substance, the range of the mass-to-charge ratio, a threshold to determine as detected, a background threshold (BG threshold) for cleaning or the like, to perform or not AND or OR with ions derived from a sample as another detection target substance or to perform NOT with ions derived from foreign substance components.

The monitor 27 displays the presence or not of the sample as the identified detection target substance and/or a result of mass spectrometry. The monitor 27, for example, illuminates a red lamp when the sample as the detection target substance is detected, illuminates a blue lamp when the sample is not detected and illuminates a yellow lamp when the result is around a threshold. A method of displaying the result is not limited to illumination of lamps, and the entire screen or a part thereof of the monitor 27 may be changed so as to allow an operator to recognize whether the substance is detected or not. Instead of visual display, sound such as a buzzer may be used for notice. Alternatively, texts or colors may be used for display indicating what is detected. The intensity of ions detected may be displayed on the screen by a bar chart or numeric values. This monitor 27 may display such information not at the main body of the system but at a monitoring center at a remote place via a network communication or the like.

Figure 4:
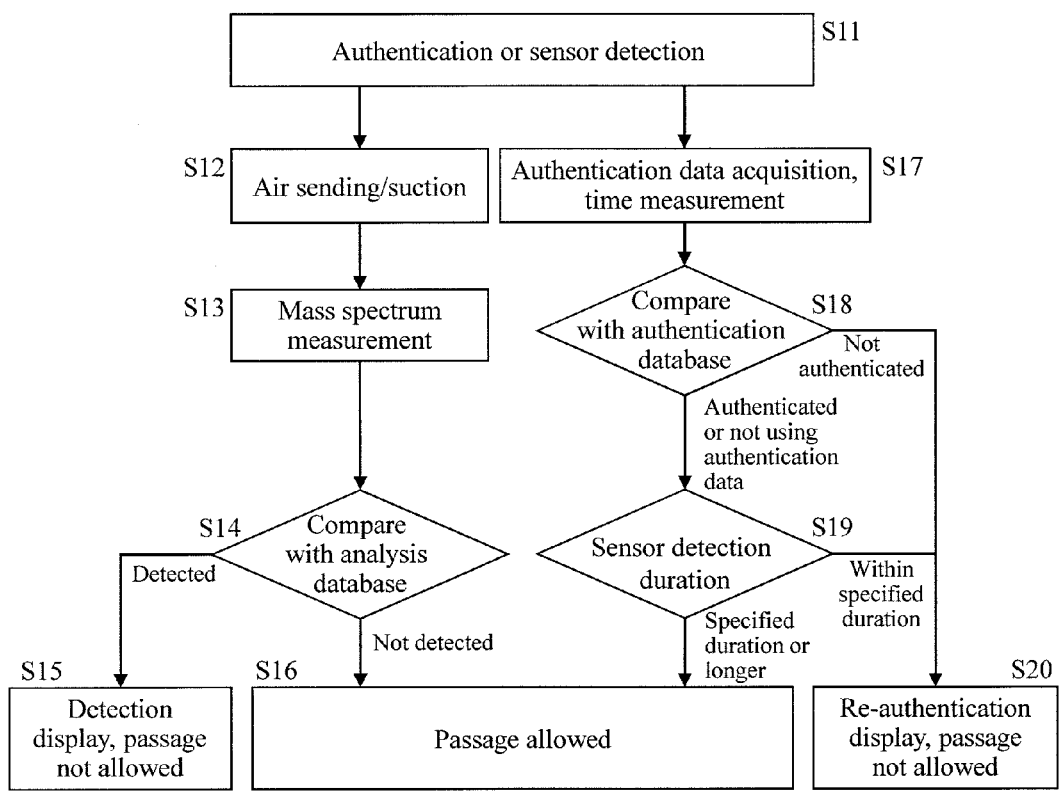
FIG. 4 shows exemplary procedure to detect a detection target substance.

FIG. 4 shows exemplary procedure to detect a detection target substance according to the present embodiment. Authentication of the authentication target 2 starts, or a hand or the like as a detection target is detected by a sensor (S11). Then, the process is divided into the process on an analysis side (S12 to S14) and the process on an authentication side (S17 to S19). On the analysis side, in parallel with the authentication side or after the authentication, gas and/or particles as a detection target substance are removed from the authentication target 2 or the hand by air flowing along the authentication plane 3, and are sucked from the introduction region (S12). The sucked gas and/or particles as a detection target substance are condensed at the sampling region 10, and then a mass spectrum of the detection target substance is analyzed at the mass analysis region 23 (S13). The analysis result is compared with a database of the mass database region 26, thus determining the presence or not of the detection target substance (S14). When the detection target substance is detected, alarm is issued to display the detection, and the passage is not allowed (S15). A method for the display may be sound or light issued as the alarm, or the detection may be reported to a security staff. Alternatively, control such as closing the gate, for example, may be performed. When no detection target substances are detected, comparison is made with the authentication result and the passage is allowed (S16).

On the other hand, on the authentication side, authentication of the authentication target 2 is performed, or a hand or the like is detected by a sensor (S11). Authentication data of the authentication target 2 is acquired (S17). Alternatively, when authentication data is not used, for example, when inspection only by urging a hand or the like to be held over the authentication plane 3 is performed, duration for holding the hand over the authentication plane 3 is measured (S17). When duration (specified duration) for authentication is decided, for instance, it is specified so that the authentication target 2 is to be held over for 2 seconds or longer, whereby duration for inspection can be secured with reliability. Next, determination is made by comparing with an authentication database registered beforehand (S18). In the case of disagreement, alarm is displayed so as to urge re-authentication, and the passage is not allowed (S20). In the case of agreement with the authentication data or when authentication data is not used, sensor detection duration is detected (S19). The specified duration for sensor detection may be 2 sec. or longer, for example. When the hand is held only for 1 sec., even when authentication is obtained, alarm is displayed because the duration is shorter than the specified duration, so as to urge re-authentication, and the passage is not allowed (S20). When it is confirmed that the authentication target 2 is held over the authentication plane 3 for the specified duration or longer, e.g., for 2 sec. or longer, then comparison is made with the analysis result and the passage is allowed (S16).

Figure 5:
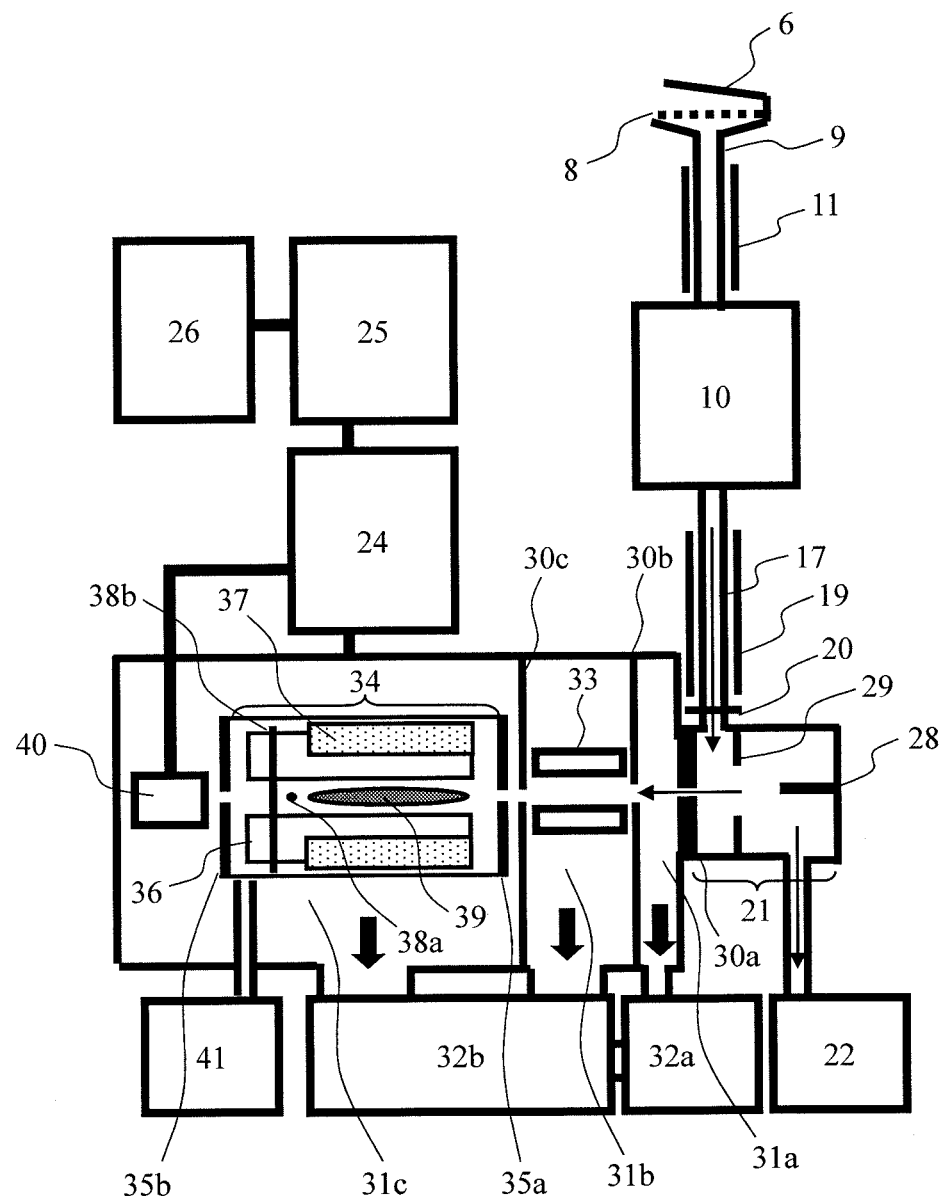
FIG. 5 shows an exemplary mass analysis region according to the present invention.

FIG. 5 schematically shows an exemplary mass analysis region of the present embodiment. The following describes an example using a wire-type linear ion trap mass spectrometer as the mass analysis region. The ion source 21 generates primary ions using corona discharge in the air, and the sample is ionized using a chemical reaction with these primary ions. The ion source 21 includes a needle electrode 28, and high voltage is applied between the needle electrode 28 and a counter electrode 29 so that corona discharge occurs in the vicinity of the front end of the needle electrode 28. For instance, 5 kV is applied for positive ionization, and −4 kV is applied for negative ionization. This corona discharge ionizes nitrogen, oxygen, water vapor and the like in the air to be primary ions. The thus generated primary ions are moved to the side of a first aperture 30*a* due to electric field. The sample sucked through the analysis pipe 17 flows into the needle electrode 28 side via the opening of the counter electrode 29. At this time, the sample reacts with primary ions, whereby the sample is ionized.

Ions of the ionized sample are introduced to an ion trap region 34 of a vacuum region 31*c* via a first aperture 30*a*, a first differential pumping region 31*a*, a second aperture 30*b*, a second differential pumping region 31*b*, and a third aperture 30*c*. Ions are introduced from air to vacuum through differential pumping. For the differential pumping, vacuum pumps 32*a*, 32*b* are used. One vacuum pump 32*b* enables vacuum pumping at two parts. The vacuum pump 32*a* is used as a roughing vacuum pump of the vacuum pump 32*b*. Differential pumping may be performed by another method of using vacuum pumps individually. The first aperture 30*a* has an aperture size of 0.12 mm in inner diameter and 10 mm in length, the second aperture 30*b* has an aperture size of 0.5 mm in inner diameter and the third aperture 30*c* has an aperture size of 1.2 mm in inner diameter. The aperture size depends on the pumping volume. The second differential pumping region 31*b* is provided with an ion guide 33. Instead of the ion guide, an ion lens may be used, for example. The first differential pumping region 31*a*, the second differential pumping region 31*b* and the vacuum region 31*c* may be provided with an ion guide, an ion lens or the like. The ion source 21, the first aperture 30*a*, the second aperture 30*b* are desirably heated to prevent dirt or the like from attaching to the inside thereof.

An ion trap region 34 includes an inlet end lens 35*a*, an outlet end lens 35*b*, quadruple rods 36, excitation electrodes 37 inserted between the quadruple rods 36, trap wire electrodes 38*a*, and extraction wire electrodes 38*b*. To the ion trap region 34, buffer gas necessary for ion trap or ionic dissociation are supplied from a gas supply unit 41. The present embodiment uses helium gas, which may be air, argon, nitrogen or the like. Ions introduced to the ion trap region 34 are trapped at a trap region 39 by electrostatic potential between the inlet end lens 35*a* and the trap wire electrodes 38*a* in the axial direction and quadruple potential by the quadruple rods 36 in the radial direction. When AC voltage is applied to the excitation electrodes 37 inserted between the quadruple rods 36, ions having specific m/z only are resonantly-excited in the direction of the excitation electrodes 37, and is discharged in the axis direction by extraction electric filed formed by the extraction wire electrodes 38*b*. These ions having specific m/z are detected by a detector 40. Resonance conditions and voltage of the electrodes are controlled by the data processor 24 so as to discharge ions of any m/z, whereby a mass spectrum can be obtained.

The measurement of a mass spectrum once is enabled in 100 milliseconds, for example. Positive ions and negative ions may be measured alternately. Specifically, after measurement of positive ions for 0.5 sec., each electrode is switched for negative-ion detection quickly, and then negative ions are measured for 0.5 sec. Then, each electrode is switched again for positive-ion detection quickly, and then positive ions are measured. Repeating this, a mass spectrum of positive ions and a mass spectrum of negative ions are measured. As a result, mass spectra of both of the positive and negative ions can be measured in 1 sec. The switching speed can be made shorter. During measurement of positive ions (or negative ions), mass spectra in different mass ranges or a plurality of spectra such as a normal mass spectrum and a tandem mass spectrum may be measured. Such switching of the measurement modes and the continuous measurement are performed under the control of the data processor 24. The measured mass spectrum is sent to the identification region 25, to which data processing such as comparison with information in the mass database of a sample as the detection target read from the mass database region 26 is performed, thus identifying the sample as the detection target. The monitor 27 displays the presence or not of the identified sample gas as the detection target and/or the result of mass analysis. Although the present embodiment uses a wire-type linear ion trap mass spectrometer at the mass analysis region, the ion trap region 34 may be of other types of mass analysis methods such as linear trap, quadruple ion trap, quadruple filter, and ion mobility.

Figure 6:
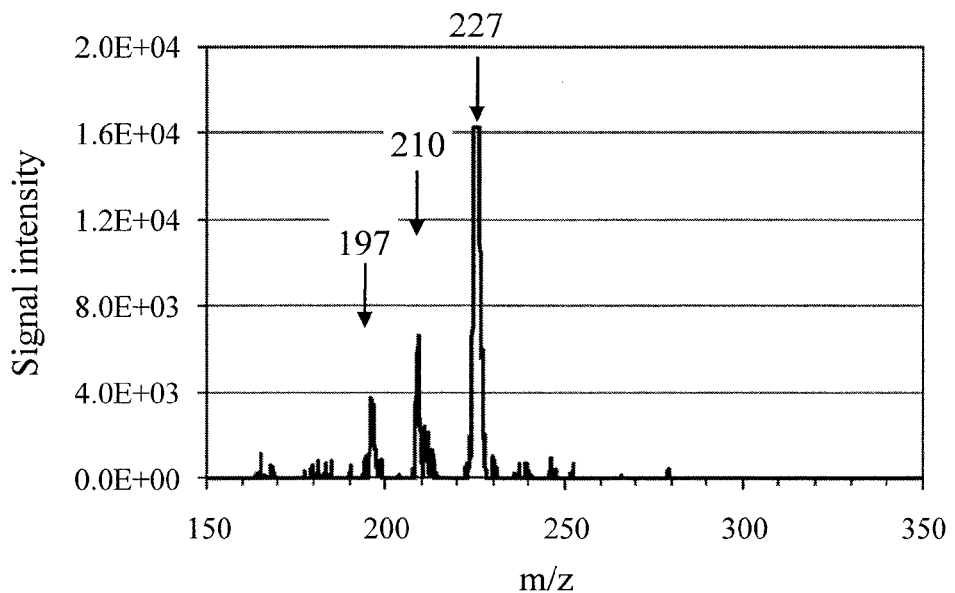
FIG. 6 shows an exemplary mass spectrum of trinitrotoluene measured by the present invention.

Trinitrotoluene that is a typical substance of an explosive component for military use was measured by the analyzer of the present embodiment. FIG. 6 shows an exemplary mass spectrum of trinitrotoluene measured by the analyzer of the present embodiment. A sample used was silica gel particles of 20 to 30 μm in size containing trinitrotoluene. A few μg of this sample was applied to an IC card as the authentication target. Then this IC card was brought into contact with the authentication plane of the analyzer for authentication, and the sample applied to the IC card was removed, which was sucked by the introduction region and was condensed at the sampling region for sampling, and was ionized at the ionization region and was analyzed at the mass analysis region. For negative ion detection, the introduction region, the pipe heater and the condensation device were heated at 120° C., the collection filter heater was heated at 200° C., and the analysis pipe heater, the ion source and the first aperture were heated at 120° C. A signal with m/z=197, 210, 227 was detected. Trinitrotoluene has a molecular mass (M) of 227. M/z=227 is estimated as (M)−. M/z=210 is estimated as (M−OH)−, and m/z=197 is estimated as (M−NO)−. When at least one of signals of m/z=197, 210 and 227 is detected, it may be determined as the detection of trinitrotoluene. Alternatively, when a plurality of peaks among m/z=197, 210 and 227 are detected, it may be determined as the detection of trinitrotoluene. This has an advantage of reducing erroneous information. For instance, when the detection is determined with the peak of m/z=227 only, such a determination may be erroneous if another component is detected at the peak of m/z=227 by accident. Instead, when it is determined as the detection of trinitrotoluene based on the simultaneous detection of at least one of m/z=197 and 210 as another peak, the possibility of erroneous information can be reduced. As other detection target substances, the detection of trimethylenetrinitramine, dinitrotoluene, cyclotetramethylenetetranitramine, pentaerythritol tetranitrate, hydrogen peroxide and the like was confirmed for negative ion detection. Then, the detection of triacetone triperoxide, hexamethylenetriperoxidediamine and the like was confirmed for positive ion detection. Tandem mass analysis further can improve selectivity while reducing an erroneous information ratio.

Figure 7:
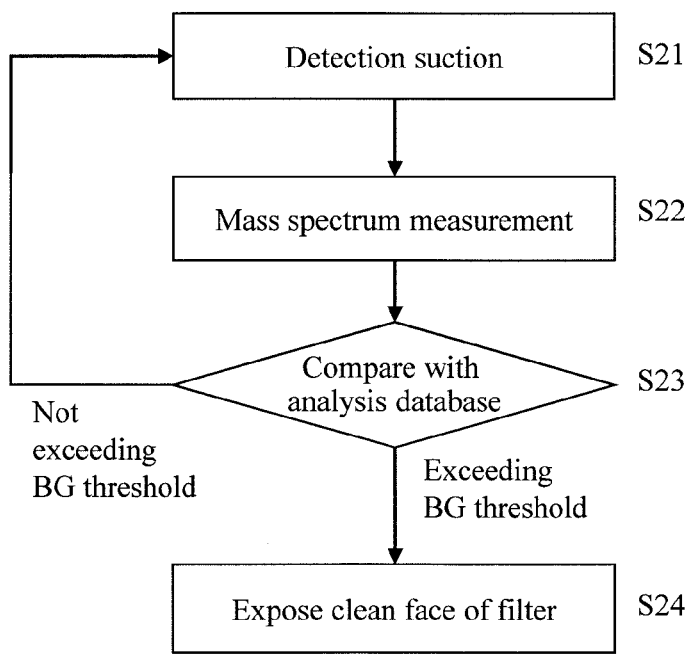
FIG. 7 shows exemplary procedure to expose a clean face of a collection filter.

FIG. 7 shows exemplary procedure to expose a clean face of the collection filter. Background (BG) of a sample is sucked from the collection filter via an analysis pipe (S21). The sucked background is ionized, and a mass spectrum thereof is analyzed at the mass analysis region (S22). A result of the analysis is compared with a database of the mass analysis region, and determination is made whether the background exceeds a BG threshold or not due to foreign substances or the like (S23). In the case of the collection filter getting dirty due to foreign substances or the like, the background will exceed the BG threshold, and then the collection filter is wound up by a predetermined amount under control of the collection filter control unit to expose a clean face thereof so that the background does not exceed the BG threshold due to foreign substances or the like (S24).

Figure 8:
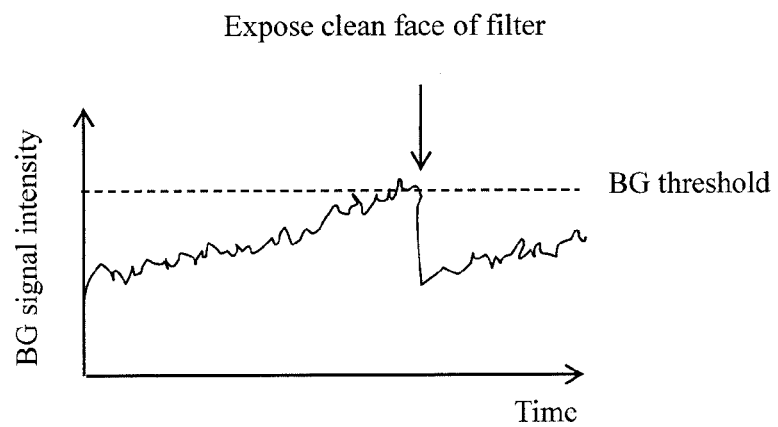
FIG. 8 shows an exemplary changing state of signal intensity of background when the operation to expose a clean face of a particle collection filter is performed.

FIG. 8 shows an exemplary changing state of signal intensity of background (BG) when the operation to expose a clean face of the particle collection filter is performed. This shows the background signal intensity change when the peak of trinitrotoluene with m/z=227 is assumed as the detection target. As the filter gets dirty over time due to foreign substances or the like, the background signal intensity tends to increase. Conversely the BG signal intensity may decrease over time in some cases, and this is due to an effect of cleaning the particle collection filter by heating or the like. When the BG signal intensity exceeds a BG threshold described in the mass database, a clean face of the collection filter is exposed. Then, the BG signal intensity suddenly decreases.

Such an operation to expose a clean face of the collection filter enables the clean face of the filter to be exposed only when the signal intensity exceeds the BG threshold or when the detection target substance is detected. This enables long period use with less amount of the filter, thus reducing maintenance frequency.

(B) Second Embodiment

The following describes second embodiment of the present invention. In the present embodiment, particles are sampled using a plurality of condensation devices at the sampling region. This method enables sampling of particles as a detection target substance while controlling their particle size.

Figure 9:
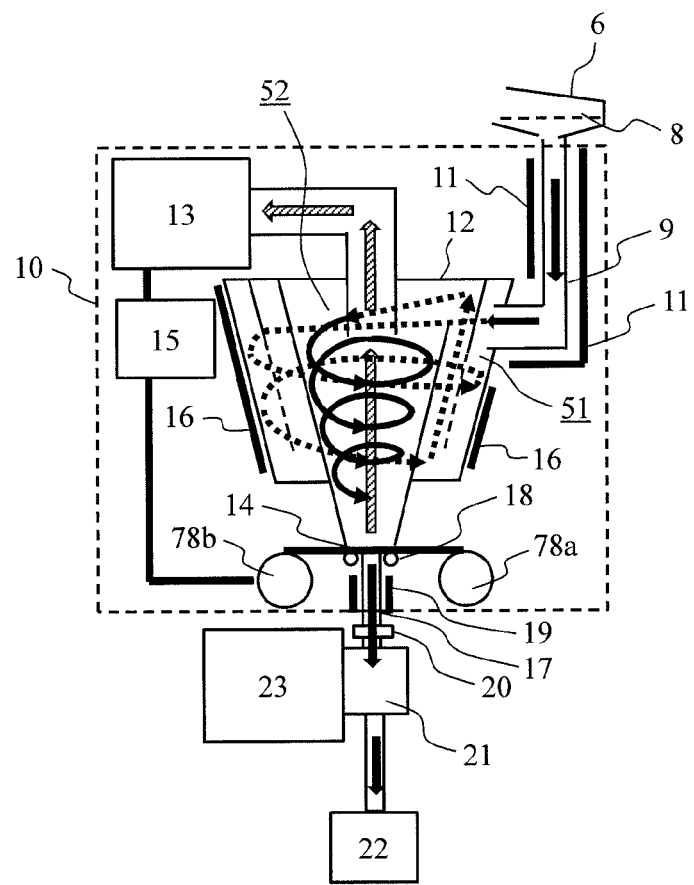
FIG. 9 shows an exemplary sampling region including a large-rotating condensation device and a small-rotating condensation device.

FIG. 9 schematically shows an exemplary sampling region including a large-rotating condensation device and a small-rotating condensation device. The sampling region 10 is provided with a conic large rotation condensation device 51 having a large rotating radius for a cyclonic effect and a conic small rotation condensation device 52 having a small rotating radius for a cyclonic effect. The small rotation condensation device 52 is connected in series with the large rotation condensation device 51 on the downstream side. Gas and/or particles as a detection target substance sucked from the introduction region 6 are firstly introduced to the large conic large rotation condensation device 51 via an introduction pipe 9. Then, a cyclonic effect having a large rotating radius occurs inside the large rotation condensation device 51, and for example, particles having size exceeding 100 μm are collected at the bottom face of the large rotation condensation device 51, and particles having a size other than that of 100 μm or less are sent to the following small conic small rotation condensation device 52. A cyclonic effect having a small rotating radius occurs inside the small rotation condensation device 52, and for example, particles having a size of 100 μm or less and 5 μm or more are collected by the collection filter 14. Particles less than 5 μm in size and the air flow are then sucked by the large intake pump 13.

Particles as the detection target substance sampled by the collection filter 14 and having a size of 100 μm or less and 5 μm or more are heated by the collection filter heater 18 for vaporization, and the vaporized sample is introduced to the ion source 21 for ionization. Then the ionized ions are subjected to mass analysis at the mass analysis region 23, thus detecting the presence or not of the detection target substance in the sample. The large rotation condensation device 51 samples relatively large particles, especially dust and the like, thus preventing the collection filter 14 from clogging. The large rotation condensation device 51 samples such dust and the like at the bottom face. Thus the large rotation condensation device 51 configured to open the bottom face easily enables discarding of the dust and the like regularly. A configuration enabling automatic discarding of the dust and the like at the bottom face at night or midnight during a non-operating state can shorten the maintenance time. A condensation device having a smaller rotating radius provided after the small rotation condensation device 52 enables sampling of particles having a smaller size.

Figure 10:
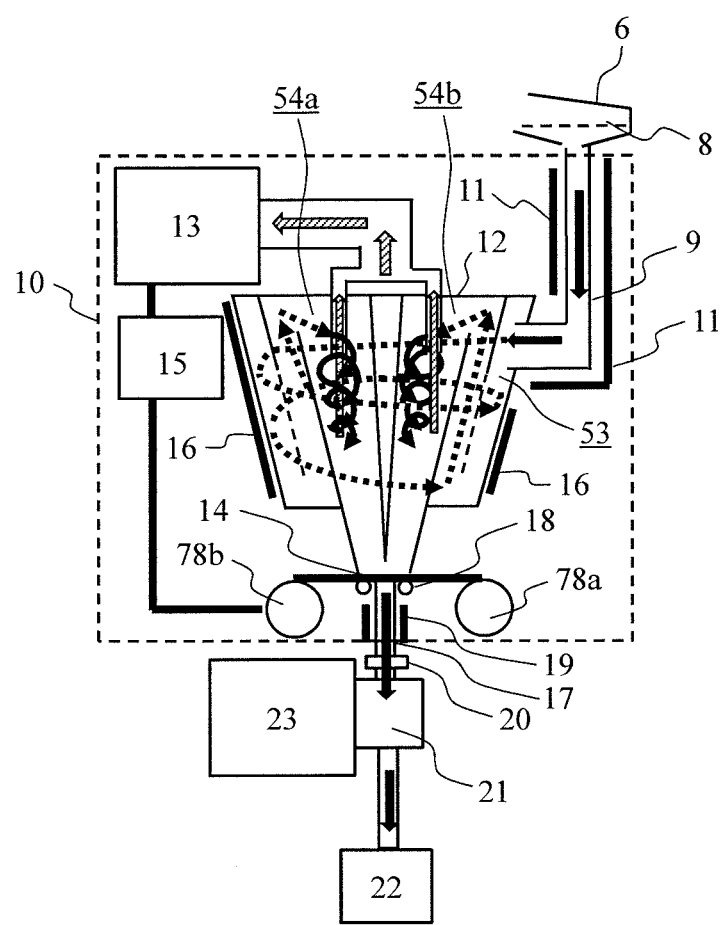
FIG. 10 shows an exemplary sampling region including a large-rotating condensation device and a plurality of small-rotating condensation devices.

FIG. 10 schematically shows an exemplary sampling region including a large-rotating condensation device and a plurality of small-rotating condensation devices. For instance, the sampling region 10 is provided with a conic large rotation condensation device 53 having a large rotating radius for a cyclonic effect and two conic small rotation condensation devices having a small rotating radius for a cyclonic effect, including a first small rotation condensation device 54a and a second small rotation condensation device 54b. They are arranged, viewed from the above, for example, so that the first small rotation condensation device 54a and the second small rotation condensation device 54b are aligned around the collection filter 14. The first small rotation condensation device 54a and the second small rotation condensation device 54b are sucked by a large intake pump 13. Gas and/or particles as a detection target substance sucked from an introduction region 6 are firstly introduced to the large conic large rotation condensation device 53 via an introduction pipe 9. Herein, a cyclonic effect having a large rotating radius occurs inside the large rotation condensation device 53, and for example, particles having size exceeding 100 μm are collected at the bottom face of the large rotation condensation device 53, and particles having a size other than that of 100 μm or less are sent to the following small conic first small rotation condensation device 54a and such a second small rotation condensation device 54b. A cyclonic effect having a small rotating radius occurs inside the first small rotation condensation device 54a and the second small rotation condensation device 54b, and for example, particles having a size of 100 μm or less and 5 μm or more are collected by the collection filter 14. Particles less than 5 μm in size and the air flow are then sucked by the large intake pump 13. Particles as the detection target substance sampled by the collection filter 14 and having a size of 100 μm or less and 5 μm or more are heated by the collection filter heater 18 for vaporization, and the vaporized sample is introduced to the ion source 21 for ionization. Then the ionized ions are subjected to mass analysis at the mass analysis region 23, thus detecting the presence or not of the detection target substance in the sample.

In this example, two of the small rotation condensation devices are used, and they may include two or more. Although the conic first small rotation condensation device 54a and second small rotation condensation device 54b have the same size in this example, they may have different rotating radiuses, whereby each device can control a different particle size for condensation. Alternatively, each device may control a different flow rate or flow amount for suction, whereby particle sizes for condensation can be controlled. Both of the rotation radius and the flow rate or the flow amount may be changed. A condensation device having a smaller rotating radius provided after the first small rotation condensation device 54a and the second small rotation condensation device 54b enables sampling of particles having a smaller size.

Figure 11:
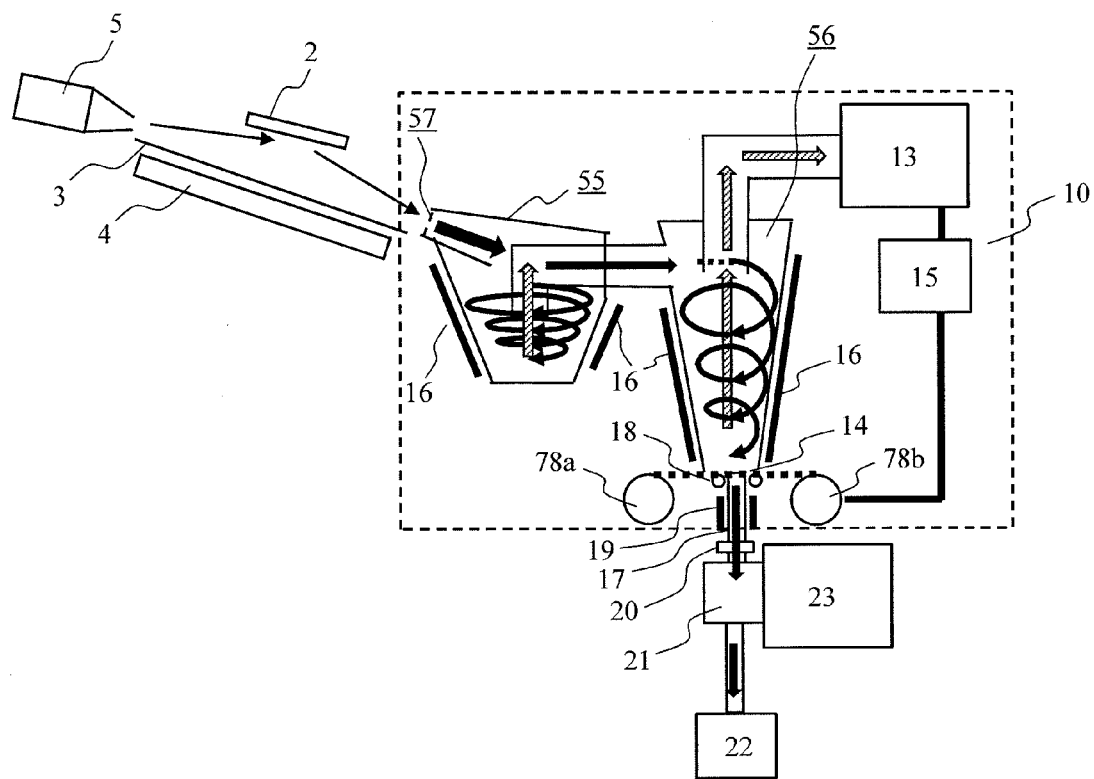
FIG. 11 shows an exemplary sampling region including a condensation introduction region and a condensation device.

FIG. 11 shows an exemplary sampling region including a condensation introduction region and a condensation device. The sampling region 10 is provided with a conic condensation introduction region 55 having a large rotating radius for a cyclonic effect, followed by a conic small rotation condensation device 56 having a smaller rotating radius than that of the condensation introduction region 55. When the authentication target 2 is brought closer to the authentication plane 3 to acquire authentication at the authentication region 4, air flow from the blowing region 5 removes gas and/or particles as a detection target substance attached to the authentication target 2. The removed gas and/or particles as a detection target substance are sucked by the condensation introduction region 55. The condensation introduction region 55 is provided with a rough mesh filter 57, thus preventing large dust or a finger from entering the condensation introduction region 55. The condensation introduction region 55 has a conic shape having a large radius, thus generating a cyclonic effect having a large rotating radius. Due to this cyclonic effect, particles having size exceeding 100 μm, for example, are collected at the bottom face of the condensation introduction region 55. Particles having a size other than that of 100 μm or less are sent to the following small conic small rotation condensation device 56. A cyclonic effect having a small rotating radius occurs inside the small rotation condensation device 56, and for example, particles having a size of 100 μm or less and 5 μm or more are collected by the collection filter 14. Particles less than 5 μM in size and the air flow are then sucked by the large intake pump 13.

Particles as the detection target substance sampled by the collection filter 14 and having a size of 100 μm or less and 5 μm or more are heated by the collection filter heater 18 for vaporization, and the vaporized sample is introduced to the ion source 21 for ionization. Then the ionized ions are subjected to mass analysis at the mass analysis region 23, thus detecting the presence or not of the detection target substance in the sample. The condensation introduction region 55 samples relatively large particles, especially dust and the like, thus preventing the collection filter 14 from clogging. The condensation introduction region 55 samples such dust and the like at the bottom face. Thus the condensation introduction region 55 configured to open the bottom face easily enables discarding of the dust and the like regularly. A configuration enabling automatic discarding the dust and the like at the bottom face at night or midnight during a non-operating state can shorten the maintenance time. A condensation device having a smaller rotating radius provided after the small rotation condensation device 56 enables sampling of particles having a smaller size. Making the rotating radius of the condensation introduction region 55 a half enables a more compact device.

Figure 12:
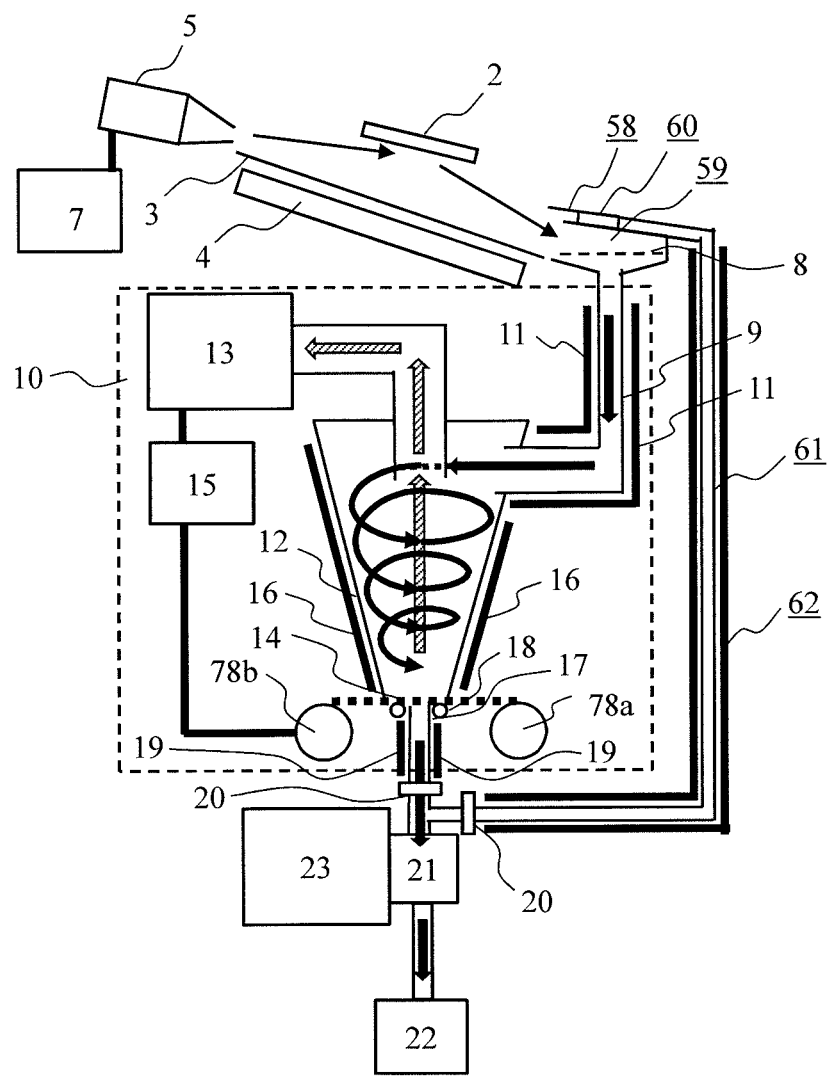
FIG. 12 shows an exemplary analyzer including a gas sampling region, a particle sampling region and a condensation device.

FIG. 12 schematically shows an exemplary analyzer including a gas sampling region, a particle sampling region and a sampling region. A particle condensation method based on a cyclonic effect may attenuate the air flow of gas and vapor. Such air flow including gas or vapor, attached to other particles, can be detected usually. Then, in order to increase the detection sensitivity of the air flow including gas or vapor, the air flow including gas or vapor is preferably collected separately from the particles condensation method. Then, this example is provided with a gas sampling region 58 configured to suck the air flow including gas or vapor and a particle sampling region 59 and a sampling region 10 configured to suck both of the particles and the air flow including gas or vapor. The gas sampling region 58 is provided with a fine mesh filter 60, thus preventing particles or the like from being sucked. The air flow including gas or vapor sucked by the gas sampling region 58 is introduced to an ion source 21 via a gas introduction pipe 61 for ionization. Then the ionized ions are subjected to mass analysis at a mass analysis region 23, thus detecting the presence or not of the detection target substance in the sample. For example, an Intake pump 22 has a flow rate of 4.0 liter/min. for suction. Then, the gas introduction pipe 61 has a flow rate of 2.0 liter/min., and the analysis pipe 17 has a flow rate of 2.0 liter/min. The gas introduction pipe 61 is heated by a gas introduction pipe heater 62, thus preventing adsorption of gas to the inside of the pipe. In one example, the gas introduction pipe heater 62 is heated at 70° C. For example, triacetone triperoxide is decomposed thermally, and so it is heated at a lower temperature. In this example, the gas sampling region 58 and the particle sampling region 59 are separately provided, and an introduction port may be provided inside of the particle sampling region 59 and vice versa. The gas introduction pipe 61 is desirably as short as possible so as to prevent gas from being adsorbed to the inside.

(C) Third Embodiment

The following describes third embodiment of the present invention. The present embodiment describes an exemplary method of incorporating an analyzer into a gate or the like.

Figure 13:
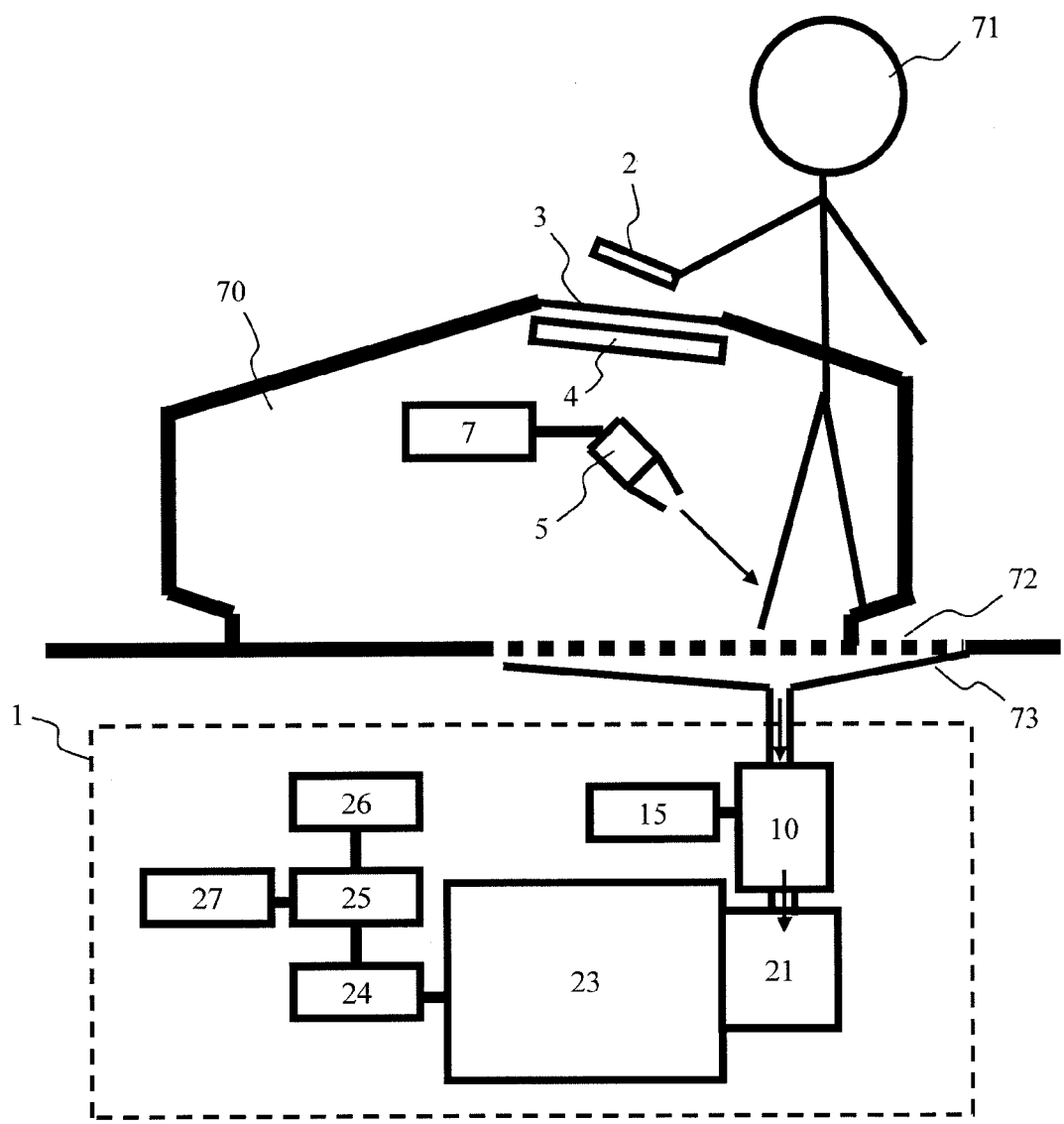
FIG. 13 schematically shows an exemplary state of an analyzer sampling particles from the below of a gate.

FIG. 13 schematically shows an exemplary state of sampling particles from the below of a gate. A gate 70 includes an authentication region 4 including an authentication plane 3, a blowing region 5 and a blowing control unit 7 built therein. Although not illustrated in this drawing, a plurality of gates may be aligned in parallel, or a single gate may be provided. A floor on which a subject 71 passes is provided with a grating 72. Below the grating 72, a bottom introduction region 73 is provided to suck particles attached to shoes or clothes of the subject 71. The grating 72 and the bottom introduction region 73 preferably have a length where the subject 71 travels while enabling authentication and identification of the authentication target 2 at the authentication region 4. When it is authenticated or the subject 71 can be identified by a passing sensor or the like, air flow is sent from the blowing region 5 to the subject 71. This air flow removes particles attached to shoes or clothes of the subject 71. The air flow may be continuous, intermittent, irregular or sporadic as long as it can remove the attached particles effectively. The blowing region 5 may be provided at any place enabling removal of particles attached to shoes or clothes by the air flow. For instance, the air flow may be applied from the below of the grating. The removed particles are condensed at a sampling region 10 and are sampled by a particle sampling filter, which are then heated for vaporization. Then, the sample is introduced to an ion source 21 from the rear face side of the particle sampling filter for ionization. The ionized ions are subjected to mass analysis at a mass analysis region 23, thus determining the presence or not of a detection target substance in the sample particles. The sampling region 10, the ion source 21, the mass analysis region 23 and the like may be configured specifically by appropriately applying the aforementioned embodiments thereto. Instead of the authentication region 4, air flow may be applied in response to a motion sensor at timing when the subject 71 passes, thus removing particles attached to shoes and clothes of the subject 71.

Figure 14:
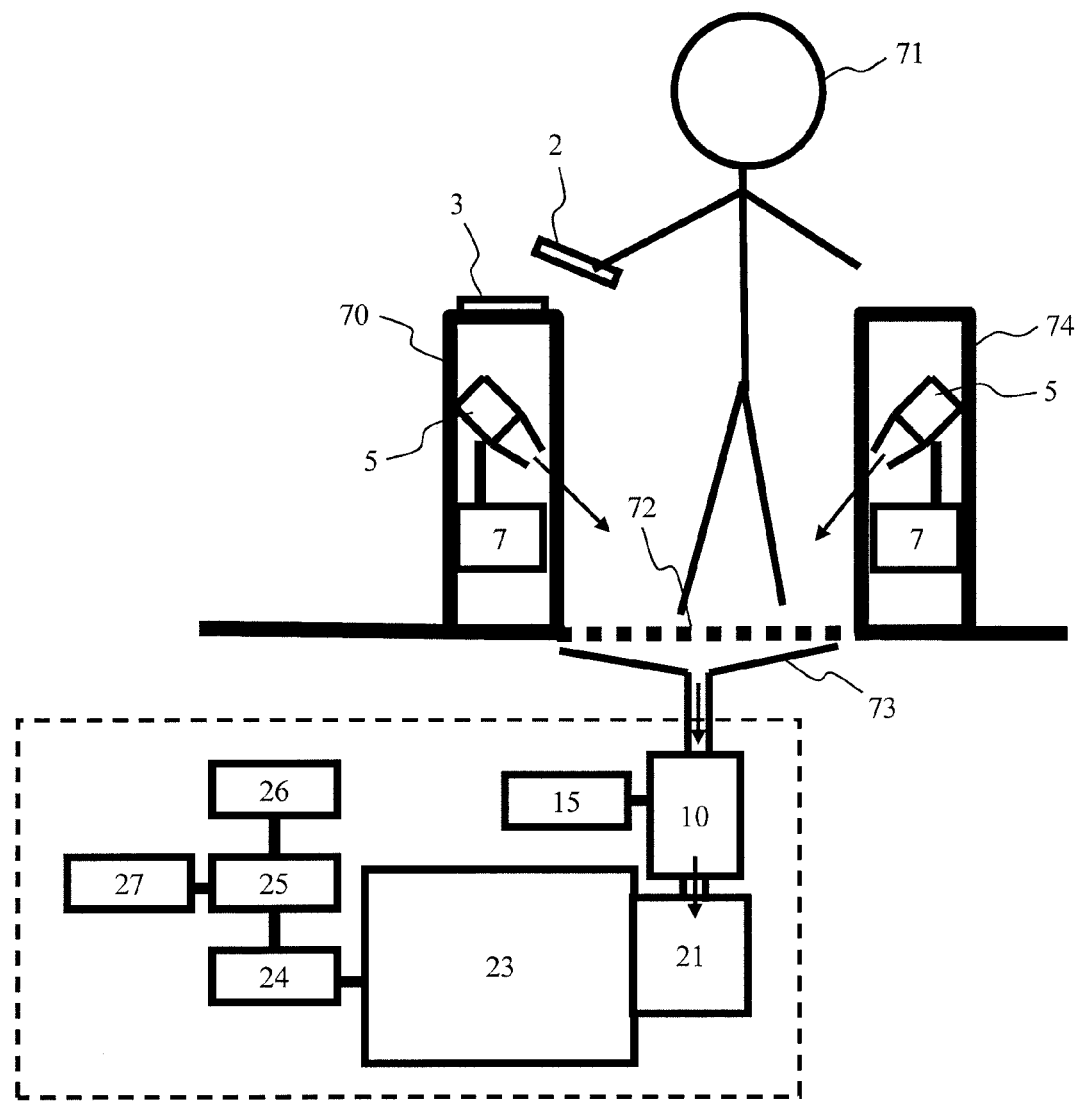
FIG. 14 is a front view showing an exemplary analyzer sampling particles from the below of the gate.

FIG. 14 is a front view showing an exemplary state of sampling particles from the below of the gate. This example shows another gate 74 provided on the opposite side of the gate 70 so that the gate 70 and the opposite side gate 74 sandwich the subject 71. Both of the gate 70 and the opposite side gate 74 apply air flow so as to remove particles attached to the subject 71. The blowing region 5 may be provided only at the gate 70 or only at the opposite side gate 74. In this example, an authentication plane 3 is provided at the gate 70 on the right side of the subject 71, which may be provided at the opposite side gate 74 on the left side. A plurality of gates may be aligned.

Figure 15:
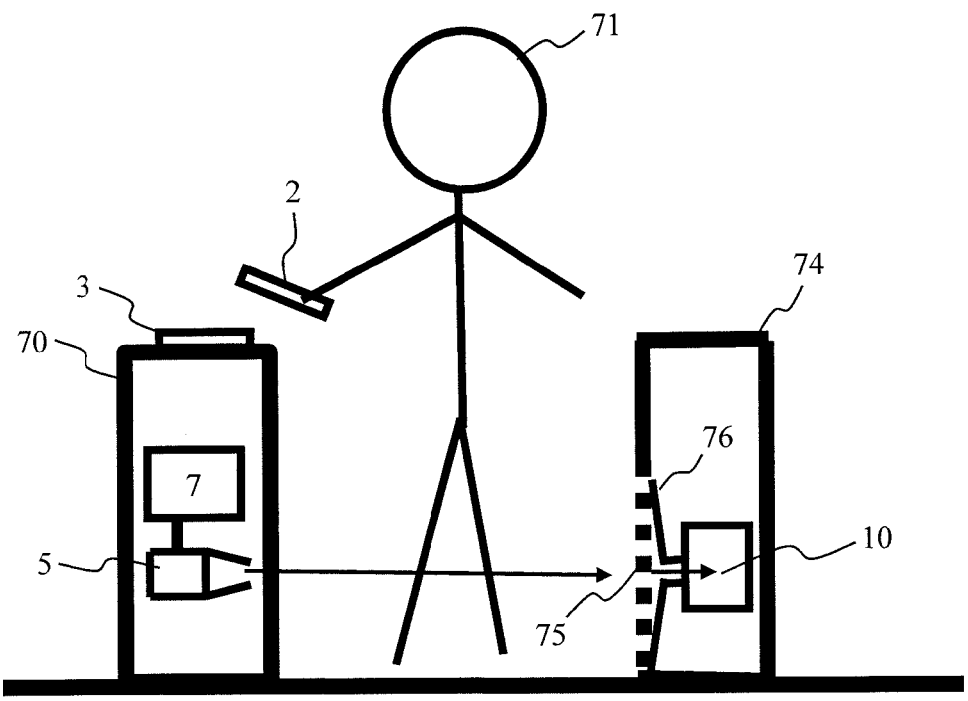
FIG. 15 is a front view showing an exemplary analyzer sampling particles from a side face of a gate FIG. 16 schematically shows an exemplary state of removing particles from an authentication target by applying air flow from the rear side of an authentication plane.

FIG. 15 is a front view schematically showing an exemplary state of sampling particles from a side face of a gate. A gate 70 is provided with a blowing region 5, and an opposite side gate 74 is provided with an introduction region 76. The introduction region 76 is covered with a protective mesh 75. The introduction region 76 is connected to a sampling region 10. Although an ion source, a mass analysis region and the like are not illustrated, they are built in the opposite side gate 74. The blowing region 5 and the introduction region 76 may be built in the opposite gates, respectively. Air flow generated from the blowing region may be in a slit form. A plurality of blowing regions may be arranged vertically or horizontally. The vertical arrangement enables removal of particles for only one subject 71. The air flow flows as a laminar flow. The air flow may flow in one direction, which leads to advantages of a cleaning effect of the space and enabling identification of the subject 71. Alternatively, the air flow may flow as downstream from the upper face, the ceiling or the like, so as to remove particles from the body as a whole. Instead of the authentication region 4, air flow may be applied in response to a motion sensor at timing when the subject 71 passes, thus removing particles attached to shoes and clothes of the subject 71.

Figure 16:
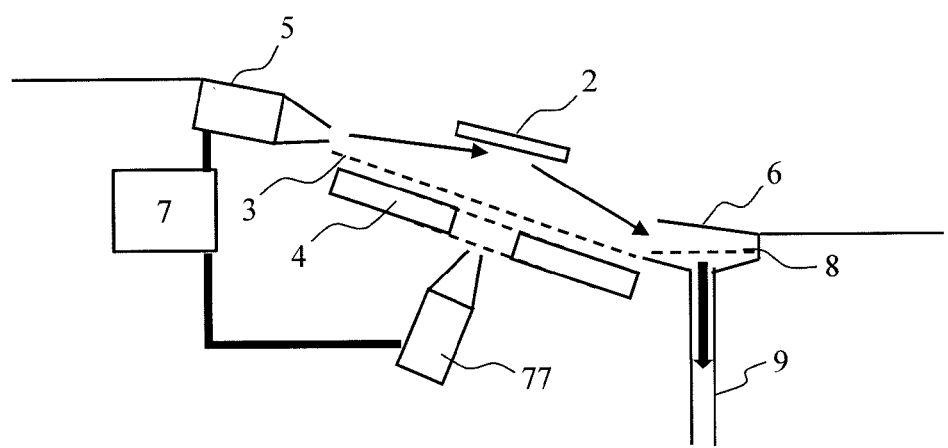

FIG. 16 schematically shows an exemplary state of removing particles from an authentication target by applying air flow from the rear side of an authentication plane. The authentication plane 3 may be in a mesh form, and a hole may be bored at a center or any position of the authentication region 4 so as not to affect the antenna of the authentication region 4. For instance, at timing when the authentication target 2 approaches and is authenticated at the authentication region 4, air flow is sent from a bottom blowing region 77 via this hole, thus removing gas and/or particles attached to the authentication target 2. Then at the removal timing, air flow is applied from the blowing region 5. The particles are sucked to the introduction region 6 along the air flow of the blowing region 5. The air flow of the blowing region 5 may be sent always or may operate in synchronization with authentication or the operation of the bottom blowing region 77. The bottom blowing region 77 only may be used without using the blowing region 5 so as to remove particles from the authentication target 2 and suck the particles to the introduction region 6.

Figure 17:
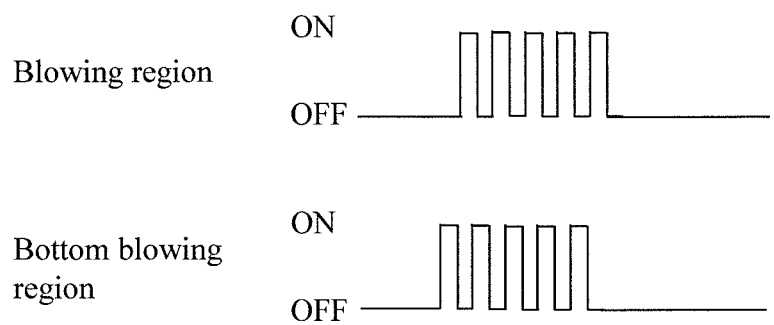
FIG. 17 shows exemplary operation sequence to remove particles from an authentication target while applying air flow from the rear of the authentication plane.

FIG. 17 shows exemplary operation sequence of the bottom blowing region and the blowing region. For instance, at timing when the authentication target 2 approaches and is authenticated at the authentication region 4, air flow is injected from the bottom blowing region 77 via the hole at injection pressure of 0.05 MPa and for injection duration of 0.1 sec., thus removing gas and/or particles attached to the authentication target 2. At timing of completing the injection from the bottom blowing region 77, air flow is injected from the blowing region 5 at injection pressure of 0.05 MPa and for injection duration of 0.1 sec., thus sucking the gas and/or particles removed by the bottom blowing region 77 to the introduction region 6. This operation is repeated 5 times, for example. Alternatively, this operation may be repeated for duration from the starting of authentication to the completion. Although not illustrated in FIG. 17, timing to start the injection may be timing when an external sensor reacts, such as a sensor to detect the approaching of an authentication target, a person, a hand, a finger or the like.

(D) Fourth Embodiment

Figure 18:
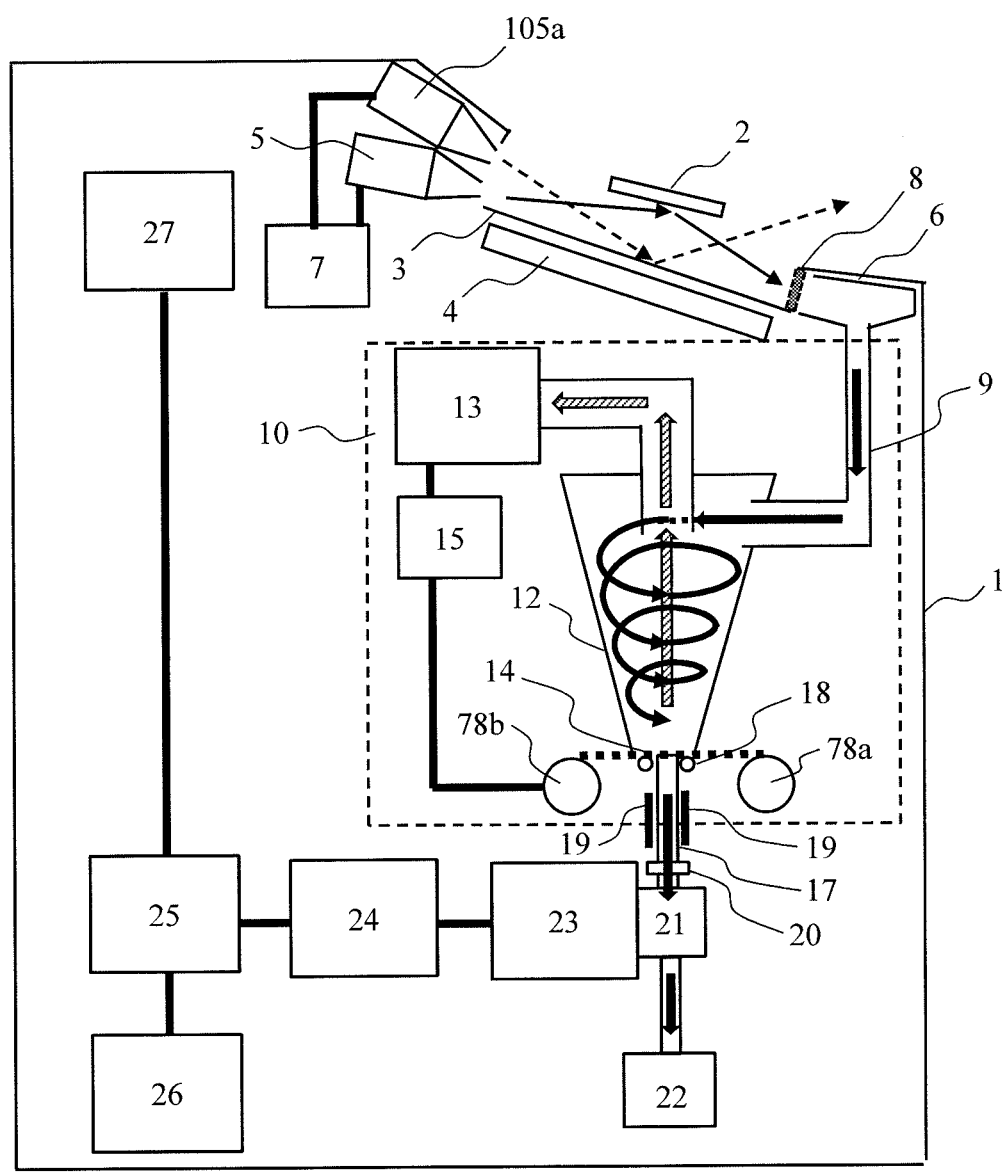
FIG. 18 schematically shows an exemplary analyzer including a blowing region to remove particles and a blowing region for cleaning, and including an introduction region to suck particles and a condensation device.

The following describes fourth embodiment of the present invention. This embodiment describes an exemplary method of cleaning an authentication plane. FIG. 18 schematically shows an exemplary analyzer including a blowing region to remove particles and a blowing region for cleaning, and including an introduction region to suck particles and a condensation device. The analyzer 1 includes an authentication region 4 having an authentication plane 3 to authenticate an authentication target 2, and so includes authentication acquisition means. The authentication plane 3 may be disposed horizontally or diagonally. The authentication plane 3 may be transparent or in a mesh form, and may have a shape letting not only electric waves but also light and air flow from the authentication region 4 pass therethrough. Authentication data obtained by authenticating the authentication target 2 is compared with authentication database provided externally or internally for determination. The blowing region 5 and an introduction region 6 are disposed so as to sandwich the authentication plane 3 therebetween. A cleaning blowing region 105a is provided on the side of the blowing region 5.

The blowing region 5 feeds air flow so as to be along the authentication plane 3, so that when the authentication target 2 approaches the authentication plane 3, the authentication target 2 comes in contact with the air flow fed, thus generating sample gas due to gas and/or particles as the detection target substance attached to the authentication target 2 or removing the gas and/or particles as the detection target substance. The wind generated from the blowing region 5 so as to remove the gas and/or particles as the detection target substance may be continuous, intermittent, irregular or sporadic. In this way, the gas and/or particles as the detection target substance removed from the authentication target 2 are transferred to the introduction region 6. This air flow is to make sure that the gas and the particles are sucked and detected without being affected by turbulent flow. The air flow is preferably fed in parallel with the authentication plane 3. That is, in order to avoid turbulent flow, the air flow is preferably fed so as not to collide with the authentication plane 3. The blowing region 5 may include an ion generator built therein so as to prevent dust from attaching or remove dust.

The cleaning blowing region 105a injects air flow to the authentication plane 3, thereby cleaning the authentication plane 3 to remove gas and/or particles as the detection target substance, which are removed from the authentication target 2 and reattaches to the authentication plane 3.

The blowing region 5 and the cleaning blowing region 105a are connected to a blowing control unit 7 to control them. The blowing control unit 7 controls the flow amount or the flow rate, the injection pressure, the temperature, the injection duration, the injection timing and the like to drive the blowing region 5 and the cleaning blowing region 105a. The blowing region 5 operates in response to a blowing region start signal. This blowing region start signal may be generated in synchronization with authentication or may be generated in response to reaction of an external sensor such as a sensor to detect the approaching of a person, a hand or a finger or a sensor to detect the passage of a person.

Figure 19:
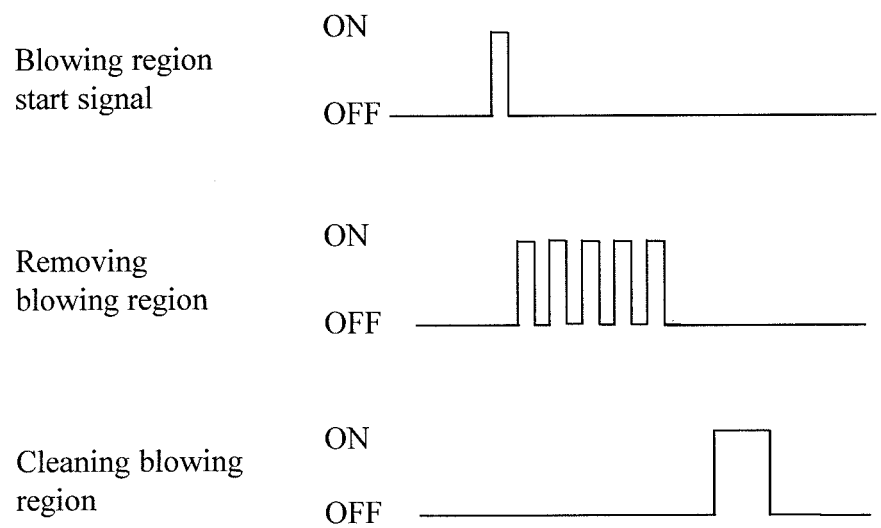
FIG. 19 shows exemplary operation sequence at a blowing region to remove particles and a blowing region for cleaning.

FIG. 19 shows exemplary operation sequence at the blowing region to remove particles and the blowing region for cleaning. In one example, after receiving a blowing region start signal, the blowing region 5 injects air flow at 0.05 MPa of injection pressure for 0.1 sec. of the injection duration, followed by break duration of 0.1 sec., which are alternately performed 5 times continuously. Thereafter, the cleaning blowing region 105a injects air flow at 0.05 MPa of injection pressure for 1 sec. of the injection duration. The injection from the cleaning blowing region 105a may be an intermittent operation similar to the blowing region 5, or may be continuous, irregular or sporadic. The cleaning blowing region 105a may include an ion generator built therein so as to prevent dust from attaching or remove dust. The injection from the cleaning blowing region 105a always operates, following the operation of the blowing region 5 to remove particles. Alternatively, it may operate after a predetermined number of times of the operation of the blowing region 5, or may operate regularly at constant time intervals, for example. After the detection target substance is detected, the cleaning blowing region 105a may operate until such a detection target substance is not detected. The blowing region 5 and the cleaning blowing region 105a may be integrated into one, and in that case, the angle may be changed mechanically or electrically between for the particle removal use and for the cleaning use. Alternatively, two nozzles having an open/close mechanism, which are set at an angle for the particle removal use and for the cleaning use may be used in one device. Particle removal and cleaning may be performed concurrently.

The transferred gas and/or particles as the detection target substance are sucked from the introduction region 6. The introduction region 6 is provided with a rough mesh filter 8, thus preventing large dust or a finger from entering the introduction region 6. The rough mesh filter 8 used may be a wire net mesh (opening: 0.5 mm, aperture ratio: 50%) as one example. This rough mesh filter 8 is exchangeable, and when the filter is clogged, the filter may be cleaned for reuse or may be exchanged with a new one.

The gas and/or particles as the detection target substance sucked from the introduction region 6 are introduced to the sampling region 10 via an introduction pipe 9. The introduction pipe 9 may be made as short as possible, or it may be omitted so that the sampling region 10 and the introduction region 6 are directly connected. The sampling region 10 includes a conic condensation device 12, a large intake pump 13, a collection filter 14 and a collection filter control unit 15. The large intake pump 13 sucks at the flow rate of 40 meter/min., for example. This suction generates a cyclonic effect inside the conic condensation device 12, so that particles of 5 μm or more in size are sampled by the collection filter 14 provided at a small-radius part of the condensation device 12, and other air flow is discharged by the large intake pump 13. The flow amount or the flow rate of the large intake pump 13 can be controlled by the collection filter control unit 15. The large intake pump 13 may always operate, or may operate in synchronization with the operation of the blowing region 5. Alternatively the large intake pump 13 may stop usually or may be controlled so as to operate when the suction amount is small.

In one example, the output of the large intake pump 13 operates during break at about 20% (flow rate of about 5 meter/sec. at the entrance of the condensation device 12), and then operates at about 80% (flow rate of about 7 to 8 meter/sec. at the entrance of the condensation device 12) that is the output of the large intake pump 13 maximizing the amount of collection of particles in synchronization with the operation of the blowing region 5, whereby particles can be collected more effectively. On the other hand, during cleaning, the output of the large intake pump 13 operates at about 100% (flow rate of about 10 meter/sec. at the entrance of the condensation device 12), whereby cleaning duration can be shortened. Such an operation can prevent the following as well, that is, the large intake pump 13 always operating at the maximum output will suck dust and the like therearound during the operation other than authentication, making the rough mesh filter 8, the collection filter 14 and the fine mesh filter 20 dirty and increasing frequency of exchange or cleaning thereof. Since such a dirty state increases background noise as well and so degrades the detection sensitivity, suction should be minimized during a non-operation state. Since the flow rate at the entrance of the condensation device 12 varies with the long diameter and the length of the cone of the condensation device 12, an optimum shape may be used.

Explosive particles typically have a size of 5 μm or more and 100 μm or less, and so particles in this range of size may be collected. The introduction region 6, the introduction pipe 9, the conic condensation device 12 and the like may have their internal faces made of Teflon or may be coated with Teflon, for example. Particles of trimethylenetrinitramine (RDX) or trinitrotoluene (TNT) as main components of plastic explosives charges negatively. Since Teflon also charges negatively, the explosive particles charging negatively have a feature of repelling and hardly being adsorbed.

The collection filter 14 is wound around a filter winding region 78b and a filter sending region 78a. The filter winding region 78b (or the filter sending region 78a as well) is controlled by the collection filter control unit 15. Although the collection filter 14 is heated by a collection filter heater 18, not only the particles that are the components as the detection target but also particles as foreign substance components are attached to the collection filter 14, and so the collection filter 14 gets dirty over time. The mass analysis region 23 always and continuously measures a mass spectrum in real time, and so can detect a change of the dirt over time. A value of a background threshold (BG threshold) is used as a threshold of this dirt, and when the dirt exceeds this value, the collection filter 14 is wound up once under the control of the collection filter control unit 15 so that a clean face is exposed. The collection filter 14 used is a ribbon-type filter having the filtering accuracy of 50 μm, the width of 10 mm and the thickness of 0.5 mm. Other than the ribbon type, a plate-type, a rope-like strand, a disk-type or a loop-type filter may be used. When the detection target substance is detected as well, the collection filter 14 may be wound up so that a clean face is exposed, whereby the next measurement can be performed promptly. The collection filter 14 may be made of stainless steel wire, metal fiber, heat-resistance fiber (e.g., cornex), glass fiber or the like.

The collection filter 14 has a rear face (the opposite side of the condensation device 12), to which an analysis pipe 17 is connected. The particles adsorbed to the collection filter 14 are heated by the collection filter heater 18. In one example, it is heated at 230° C. The heated particles are evaporated, and the sample in a gaseous form is then introduced to the ion source 21 via the analysis pipe 17 by an intake pump 22. For example, the intake pump 22 sucks at the flow rate of 0.5 liter/min. The analysis pipe 17 is heated by an analysis pipe heater 19, thus preventing adsorption of gas to the inside of the pipe. For instance, the analysis pipe heater 19 is heated at 180° C. The analysis pipe 17 and the analysis pipe heater 19 may be made as short as possible, or they may be omitted so that the collection filter 14 and the ion source 21 are directly connected. The analysis pipe 17 is provided with a fine mesh filter 20, thus preventing the ion source 21 from getting dirty due to particles that are not gasified at the collection filter 14. The fine mesh filter 20 used may be a stainless steel wire filer or a sintered body filter having filtering accuracy of 1 μm, for example. The fine mesh filter 20 may be cleaned for reuse or may be replaced with a new one if needed.

The ion source 21 used may be an atmospheric pressure chemical ionization source using negative corona discharge or positive corona discharge described in JP 2000-28579 A, for example. Ions may be generated by methods such as radiation from a radiation source, irradiation with electrons, light or laser light, penning discharge, glow discharge, barrier discharge and electrospray.

Ions generated from the sample at the ion source 21 are subjected to mass analysis at the mass analysis region 23. The mass analysis region 23 used may be a wire-type linear ion trap mass spectrometer, for example. The mass analysis may be performed by methods such as a linear ion trap mass spectrometer, a quadruple ion trap mass spectrometer, a quadruple filter mass spectrometer, a triple quadruple mass spectrometer, a time-of-flight mass spectrometer, a magnetic sector-type mass spectrometer, and ion mobility.

A signal obtained at the mass analysis region 23 is measured by the data processor 24 as a mass spectrum. Then, the peaks of mass numbers of the sample are extracted from this mass spectrum. The mass database region 26 holds information containing reference mass analysis data necessary to identify the sample. The information held includes a value of mass-to-charge ratio (m/z) that is the value obtained by dividing the mass number m of ions by the valence z of the ions as well as a relative intensity. The mass spectrum measured at the mass analysis region 23 is sent to the identification region 25, for which data processing such as comparison with data read from the mass database region 26 is performed, thus identifying the sample.

Figure 20:
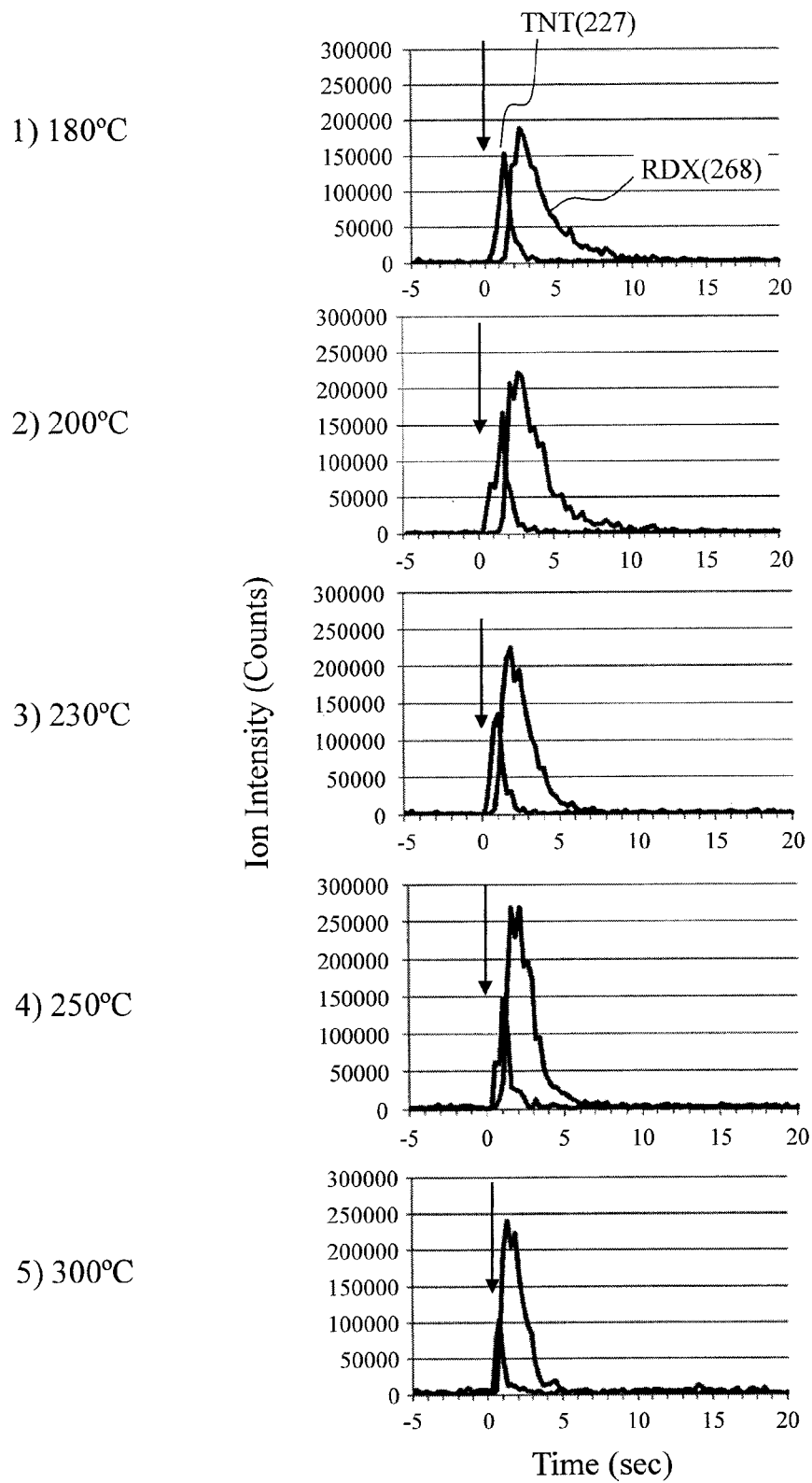
FIG. 20 shows an example of detection of trinitrotoluene and trimethylenetrinitramine while changing the heating temperature of a collection filter heater.

Trinitrotoluene and trimethylenetrinitramine that are typical substances of explosive components for military use were measured by the analyzer of the present embodiment. FIG. 20 shows an example of detection of trinitrotoluene (TNT) and trimethylenetrinitramine (RDX) while changing the heating temperature of the collection filter heater. A sample used was silica gel particles of 20 to 30 μm in size containing trinitrotoluene and trimethylenetrinitramine. A few μg of this sample was applied to an IC card as the authentication target. Then this IC card was brought into contact with the authentication plane of the analyzer of the present embodiment for authentication, and the sample applied to the IC card was removed, which was sucked by the introduction region 6 and was condensed at the condensation devices 12 for sampling, and was ionized at the ion source 21 and was analyzed at the mass analysis region 23. For negative ion detection, the analysis pipe heater 19, the ion source 21 and the first aperture were heated at 180° C. A signal with m/z=197, 210, 227 was detected for trinitrotoluene. Trinitrotoluene has a molecular mass (M) of 227. M/z=227 is estimated as (M)–. M/z=210 is estimated as (M–OH)–, and m/z=197 is estimated as (M–NO)–. Black lines in FIG. 20 represent a change of the signal of m/z=227 for trinitrotoluene over time. For trimethylenetrinitramine, a signal with m/z=269,310 was detected. Trimethylenetrinitramine has a molecular mass (M) of 222. M/z=268 is estimated as the $NO_2$ additional peak of (M+$NO_2$)–, and m/z=310 is estimated as the lactic acid additional peak of (M+La)–. Gray lines in FIG. 20 represent a change of the signal of m/z=268 for trimethylenetrinitramine over time.

Since trimethylenetrinitramine has lower vapor pressure than trinitrotoluene, trimethylenetrinitramine repeats re-adsorption and desorption to the pipe before it reaches the ion source 21, and so trimethylenetrinitramine is detected later. When the heating temperature of the collection filter heater 18 is within the range of 180° C. to 300° C., then both of trinitrotoluene and trimethylenetrinitramine can be detected within 3 sec. Further, as other detection target substances, the detection of dinitrotoluene, cyclotetramethylenetetranitramine, pentaerythritol tetranitrate, hydrogen peroxide and the like was confirmed for negative ion detection. Then, the detection of triacetone triperoxide, hexamethylenetriperoxidediamine and the like was confirmed for positive ion detection.

Figure 21:
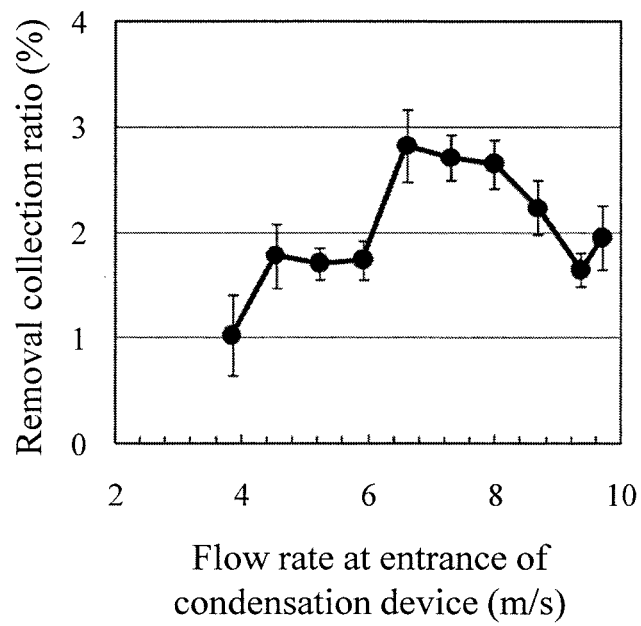
FIG. 21 shows example evaluation of a removal collection ratio of trinitrotoluene while changing the flow rate at the entrance of the condensation device.

Using a particle sample containing trinitrotoluene, a removal collection ratio was evaluated while changing the flow rate at the entrance of the condensation device 12. FIG. 21 shows example evaluation of the removal collection ratio of trinitrotoluene (TNT) while changing the flow rate at the entrance of the condensation device 12. A sample used was silica gel particles of 20 to 30 μm in size containing trinitrotoluene. A few μg of this sample was applied to an IC card as the authentication target. Then this IC card was brought into contact with the authentication plane of the analyzer of the present embodiment, and the sample applied to the IC card was removed, which was sucked by the introduction region 6 and was condensed at the condensation devices 12 for sampling, and was ionized at the ion source 21 and was analyzed at the mass analysis region 23. For negative ion detection, the collection filter heater 18 was heated at 200° C., and the analysis pipe heater 19, the ion source 21 and the first aperture were heated at 180° C. For trinitrotoluene, a signal with m/z=227 was detected. A signal obtained when the same amount as applied to the IC card is directly input to the collection filter 14 was set as 100%, and the ratio of the signal amount when it was collected at the condensation device 12 was the removal collection ratio. When the flow rate at the entrance of the condensation device 12 was about 7 to 8 meter/sec., the removal collection ratio was high, and it was confirmed that the particle sample containing trinitrotoluene of 20 to 30 μm in size was effectively collected in this range.

Figure 22:
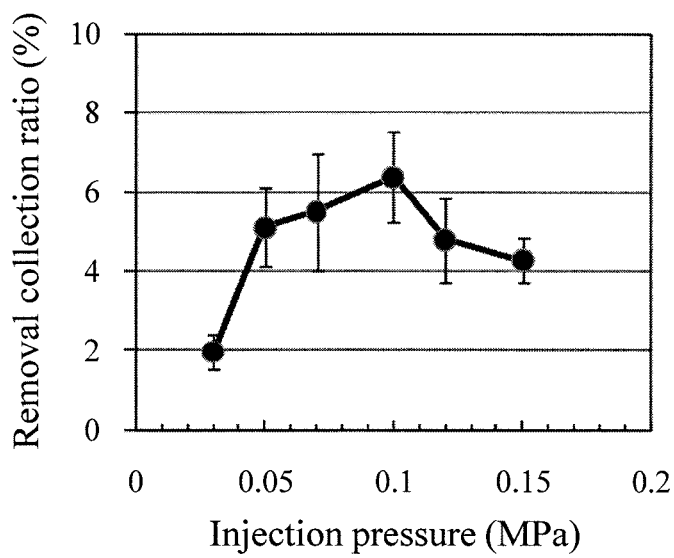
FIG. 22 shows example evaluation of the removal collection ratio of trinitrotoluene while changing the injection pressure of the blowing region.

Using a particle sample containing trinitrotoluene, a removal collection ratio was evaluated while changing the injection pressure of the blowing region 5. FIG. 22 shows example evaluation of the removal collection ratio of trinitrotoluene (TNT) while changing the injection pressure of the blowing region. Injection for 0.1 sec. of the injection duration and break for 0.1 sec. for break duration were alternately performed 5 times continuously. The removal collection ratio was favorably high in the range of the injection pressure of 0.05 to 0.1 MPa.

Figure 23:
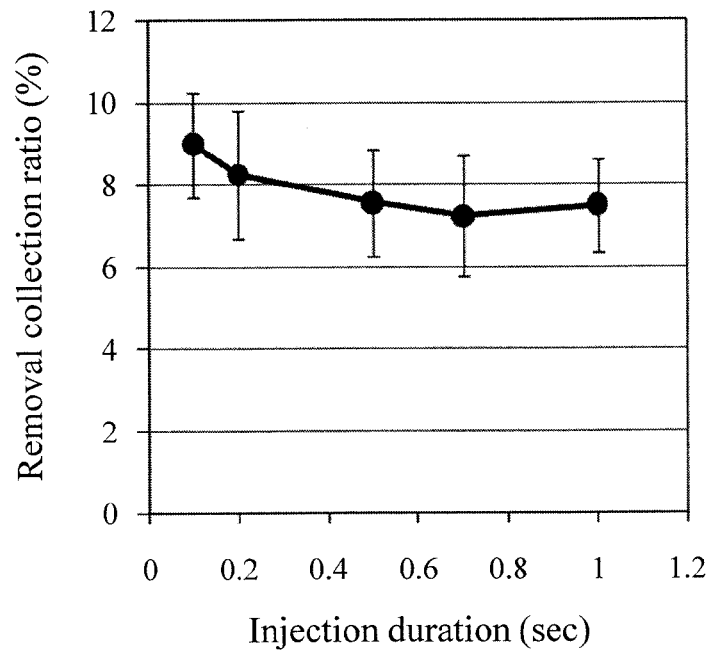
FIG. 23 shows example evaluation of the removal collection ratio of trinitrotoluene while changing the injection duration of the blowing region.

Using a particle sample containing trinitrotoluene, a removal collection ratio was evaluated while changing the injection duration of the blowing region 5. FIG. 23 shows example evaluation of the removal collection ratio of trinitrotoluene (TNT) while changing the injection duration of the blowing region. Injection at the injection pressure of 0.05 MPa and break for 0.1 sec. for break duration were alternately performed 5 times continuously. The removal collection ratio was favorably high in the range of the injection duration of 0.1 to 0.2 sec.

Figure 24:
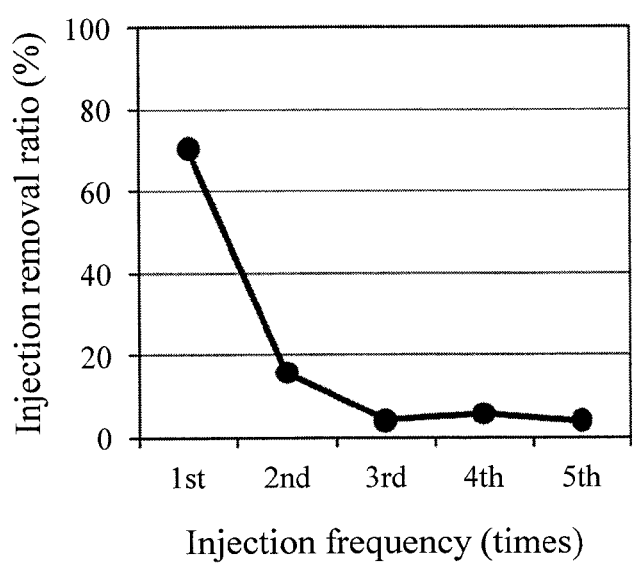
FIG. 24 shows example evaluation of the injection removal ratio of trinitrotoluene while changing the injection frequency of the blowing region.

Using a particle sample containing trinitrotoluene, an injection removal ratio was evaluated while changing the injection frequency of the blowing region 5. FIG. 24 shows example evaluation of the injection removal ratio of trinitrotoluene (TNT) while changing the injection frequency of the blowing region. Injection at the injection pressure of 0.05 MPa and for 0.1 sec. of injection duration were performed 5 times at time intervals of 5 sec. Assuming that the particle sample is removed 100% from the surface of the IC card by injection from the blowing region 5 5 times, an injection removal ratio for injection once was found based on signal intensity. The injection once yielded the injection removal ratio of about 70%, the injection twice yielded about 20%, and the injection three to five times yielded about 5%. In this way, only injection once can remove about 70% of particles, and the increased number of continuous injection enables removal of more particle sample from the IC card favorably.

Figure 25:
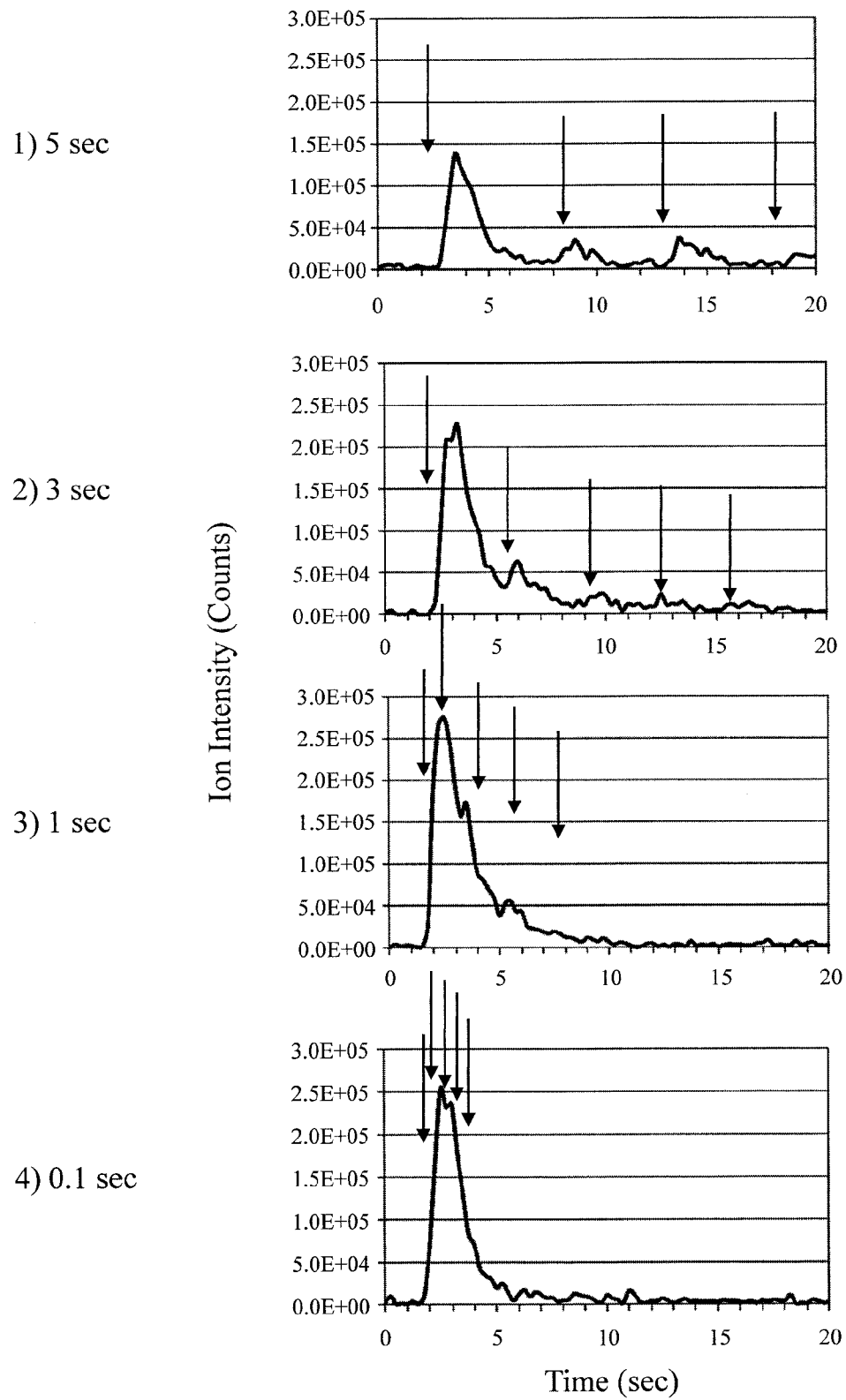
FIG. 25 shows example evaluation of the removal collection ratio of trinitrotoluene while changing the break duration of the blowing region.

Using a particle sample containing trinitrotoluene, a removal collection ratio was evaluated while changing the break duration of the blowing region 5. FIG. 25 shows example evaluation of the removal collection ratio of trinitrotoluene (TNT) while changing the break duration of the blowing region. Injection at the injection pressure of 0.05 MPa and for 0.1 sec. of injection duration were performed 5 times. When injection was performed while setting the break duration of the blowing region 5 at time intervals of 5 sec., the entire particle sample was not removed from the IC card surface in the first removal. On the other hand, the break duration at time intervals of 0.1 sec. or less enabled the removal of the entire particle sample and an increase in signal intensity also was confirmed. Even in the case of particles attached to various positions of the IC card surface, a plurality of times of injection from the blowing region 5 increases the probability of the particle sample attached to the various positions coming in contact with the air flow as the IC card is moved for authentication, thus improving the removal collection ratio favorably.

(E) Fifth Embodiment

Figure 26:
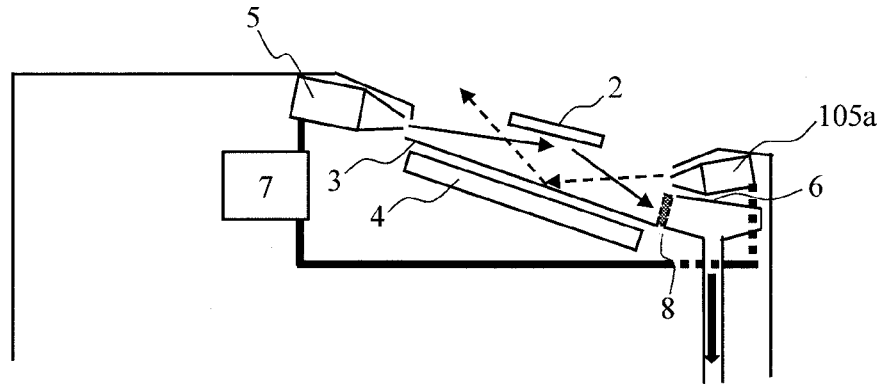
FIG. 26 schematically shows one example where a blowing region for cleaning is provided on the side of an introduction region for sucking particles.

The following describes fifth embodiment of the present invention. This embodiment describes an exemplary method of arranging a blowing region for cleaning. FIG. 26 schematically shows one example where the blowing region for cleaning is provided on the side of an introduction region for sucking particles. The blowing region 5 and the introduction region 6 are arranged so as to sandwich an authentication plane 3 therebetween. The cleaning blowing region 105a is provided on the side of the introduction region 6. The cleaning blowing region 105a injects air flow to the authentication plane 3, thus cleaning gas and/or particles removed from an authentication target 2 and reattached to the authentication plane 3. The cleaning blowing region 105a provided on the introduction region 6 side prevents the gas and/or particles as a detection target substance reattached to the authentication plane 3 from entering the introduction region 6 and so preventing contamination of the introduction region 6.

The blowing region 5 and the cleaning blowing region 105a are connected to a blowing control unit 7 to control them. The blowing control unit 7 controls the flow amount or the flow rate, the injection pressure, the temperature, the injection duration, the injection timing and the like to drive the blowing region 5 and the cleaning blowing region 105a. The blowing region 5 operates in response to a blowing region start signal. This blowing region start signal may be generated in synchronization with authentication or may be generated in response to reaction of an external sensor such as a sensor to detect the approaching of a person, a hand or a finger or a sensor to detect the passage of a person.

In one example, after receiving a blowing region start signal, the blowing region 5 injects air flow at 0.05 MPa of injection pressure for 0.1 sec. of the injection duration, followed by break duration of 0.1 sec. which are alternately performed 5 times continuously. Thereafter, the cleaning blowing region 105a injects air flow at 0.05 MPa of injection pressure for 1 sec. of the injection duration. The injection from the cleaning blowing region 105a may be an intermittent operation similar to the blowing region 5, or may be continuous, irregular or sporadic. The injection from the cleaning blowing region 105a always operates, following the operation of the blowing region 5 to remove particles. Alternatively, it may operate after a predetermined number of times of the operation of the blowing region 5, or may operate regularly at constant time intervals, for example. After the detection target substance is detected, the cleaning blowing region 105a may operate until such a detection target substance is not detected.

Figure 27:
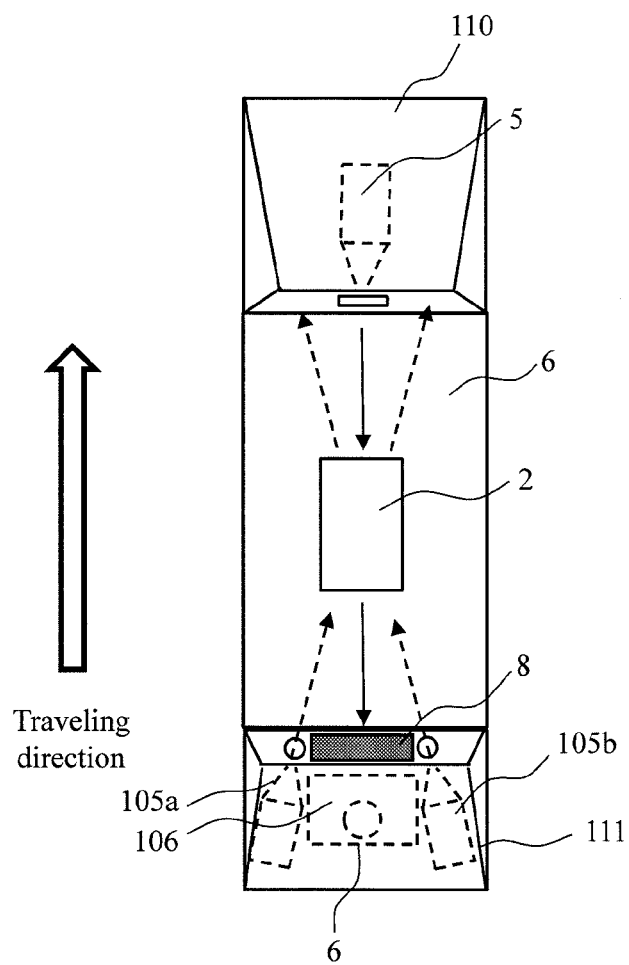
FIG. 27 shows an exemplary top view of a blowing region to remove particles, an introduction region to suck particles and a blowing region for cleaning.

FIG. 27 shows an exemplary top view of the blowing region to remove particles, the introduction region to suck particles and the blowing region for cleaning. This drawing shows an example including a plurality of blowing regions for cleaning provided at a side face on the side of the introduction region to suck particles. The blowing region 5 to remove particles is provided in a blowing cover 110. The cleaning blowing regions 105a, 105b and the introduction region 6 to suck particles are provided in an introduction cover 111. This example includes two cleaning blowing regions, which may be three or more or one. In the case of one, only the cleaning blowing region 105a is used preferably so as to inject air flow to the direction away from the traveling direction of a person. The cleaning blowing regions 105a, 105b provided at the side face of the introduction region 6 leads to an advantage of reducing the height of the introduction cover 111.

Figure 28:
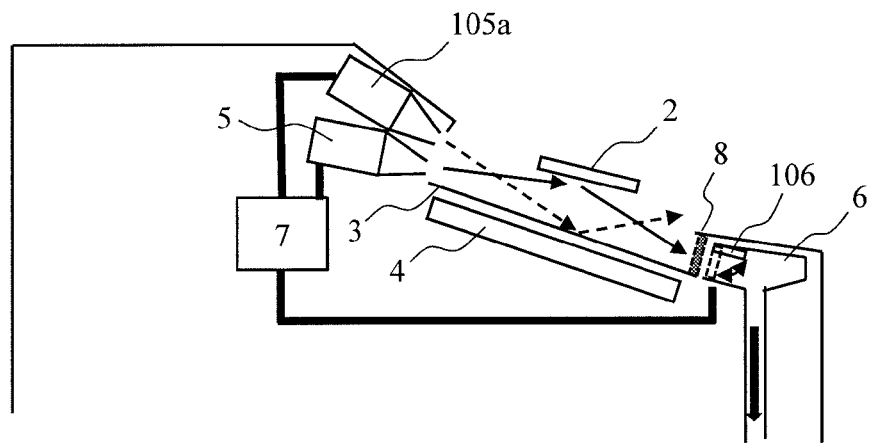
FIG. 28 schematically shows an example provided with a blowing region to remove particles, a blowing region for cleaning and an introduction region to suck particles, the introduction region being provided with a cover.

FIG. 28 schematically shows an example provided with a blowing region to remove particles, a blowing region for cleaning and an introduction region to suck particles, the introduction region being provided with a cover. A sampling cover 106 that is the cover for the introduction region is provided, whereby the closing of the sampling cover 106 can prevent the contamination of the introduction region 6 during cleaning and can prevent dust and the like from entering during a non-detecting state. The sampling cover 106 may be opened/closed mechanically or electrically, or may be opened/closed back and forth or up and down. The opening/closing of the sampling cover 106 is controlled by the blowing control unit 7. The cleaning blowing region 105a may be provided on the side of the introduction region 6.

Figure 29:
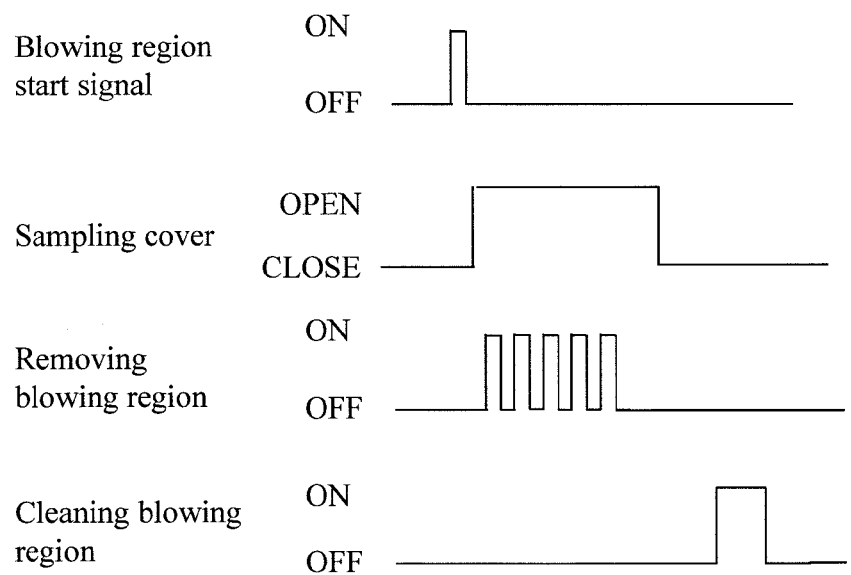
FIG. 29 shows exemplary operation sequence at a blowing region to remove particles, a cover for introduction region, and a blowing region for cleaning.

FIG. 29 shows exemplary operation sequence at the blowing region to remove particles, the sampling cover, and the blowing region for cleaning. In one example, after receiving a blowing region start signal, the sampling cover 106 is opened, and the blowing region 5 injects air flow at 0.05 MPa of injection pressure for 0.1 sec. of the injection duration, followed by break duration of 0.1 sec., which are alternately performed 5 times continuously. In predetermined duration after the injection from the blowing region 5, the sampling cover 106 is closed. For instance, after 5 sec., the sampling cover 106 is closed. Thereafter, the cleaning blowing region 105a injects air flow at 0.05 MPa of injection pressure for 1 sec. of the injection duration. The injection from the cleaning blowing region 105a may be an intermittent operation similar to the blowing region 5, or may be continuous, irregular or sporadic. The injection from the cleaning blowing region 105a always operates, following the operation of the blowing region 5 to remove particles. Alternatively, it may operate after a predetermined number of times of the operation of the blowing region 5, or may operate regularly at constant time intervals, for example. After the detection target substance is detected, the cleaning blowing region 105a may operate until such a detection target substance is not detected.

Figure 30:
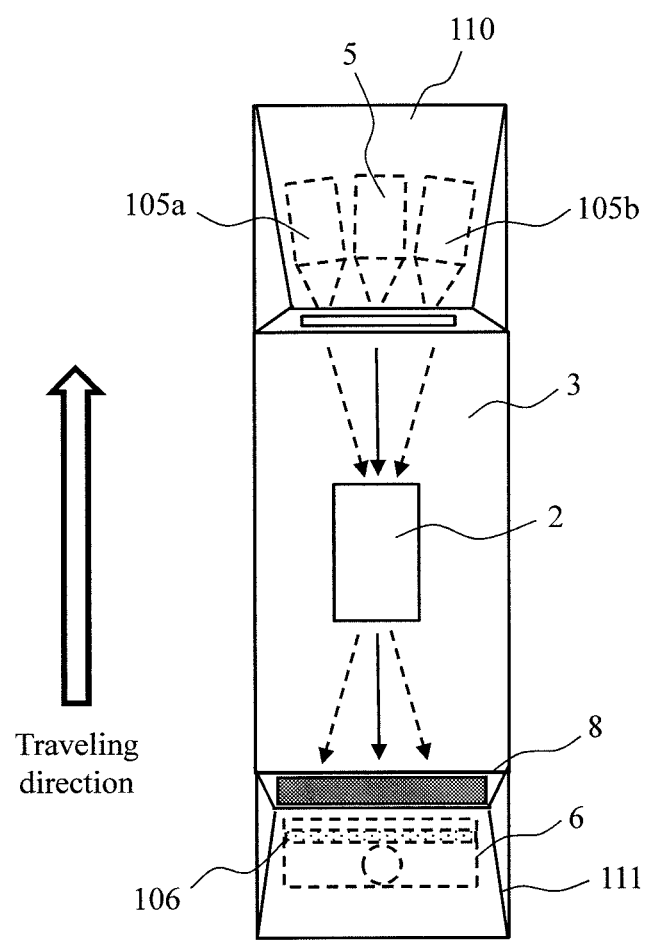
FIG. 30 shows an exemplary top view of a blowing region to remove particles, a plurality of cleaning blowing regions and an introduction region provided with a cover to suck particles.

FIG. 30 shows an exemplary top view of a blowing region to remove particles, a plurality of cleaning blowing regions and an introduction region provided with a cover to suck particles. The blowing region 5 to remove particles and the plurality of cleaning blowing regions 105a, 105b are provided in a blowing cover 110. The introduction region 6 to suck particles having a sampling cover 106 as the cover for the introduction region is provided in an introduction cover 111. This example includes two cleaning blowing regions, which may be three or more or one. In the case of one, only the cleaning blowing region 105a is used preferably so as to inject air to the direction away from the traveling direction of a person.

Figure 31:
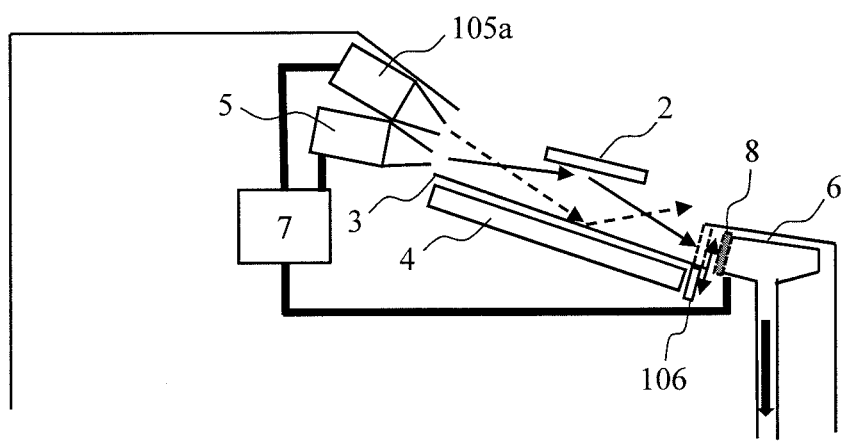
FIG. 31 schematically shows an example provided with a blowing region to remove particles, a blowing region for cleaning and an introduction region provided with a cover to suck particles, as well as a rough mesh filter provided between the cover for introduction region and the introduction region.

FIG. 31 schematically shows an example provided with a blowing region to remove particles, a blowing region for cleaning and an introduction region provided with a cover to suck particles, as well as a rough mesh filter provided between the cover for introduction region and the introduction region. The rough mesh filter 8 is provided inside of the sampling cover 106 so as to close the sampling cover 106 during a non-detection state, thereby preventing clogging of the rough mesh filter 8 due to dust and the like from the surrounding. Although not illustrated, a net may be provided before the sampling cover 106 to prevent a hand, a finger, an IC card or the like from being caught.

(F) Sixth Embodiment

Figure 32:
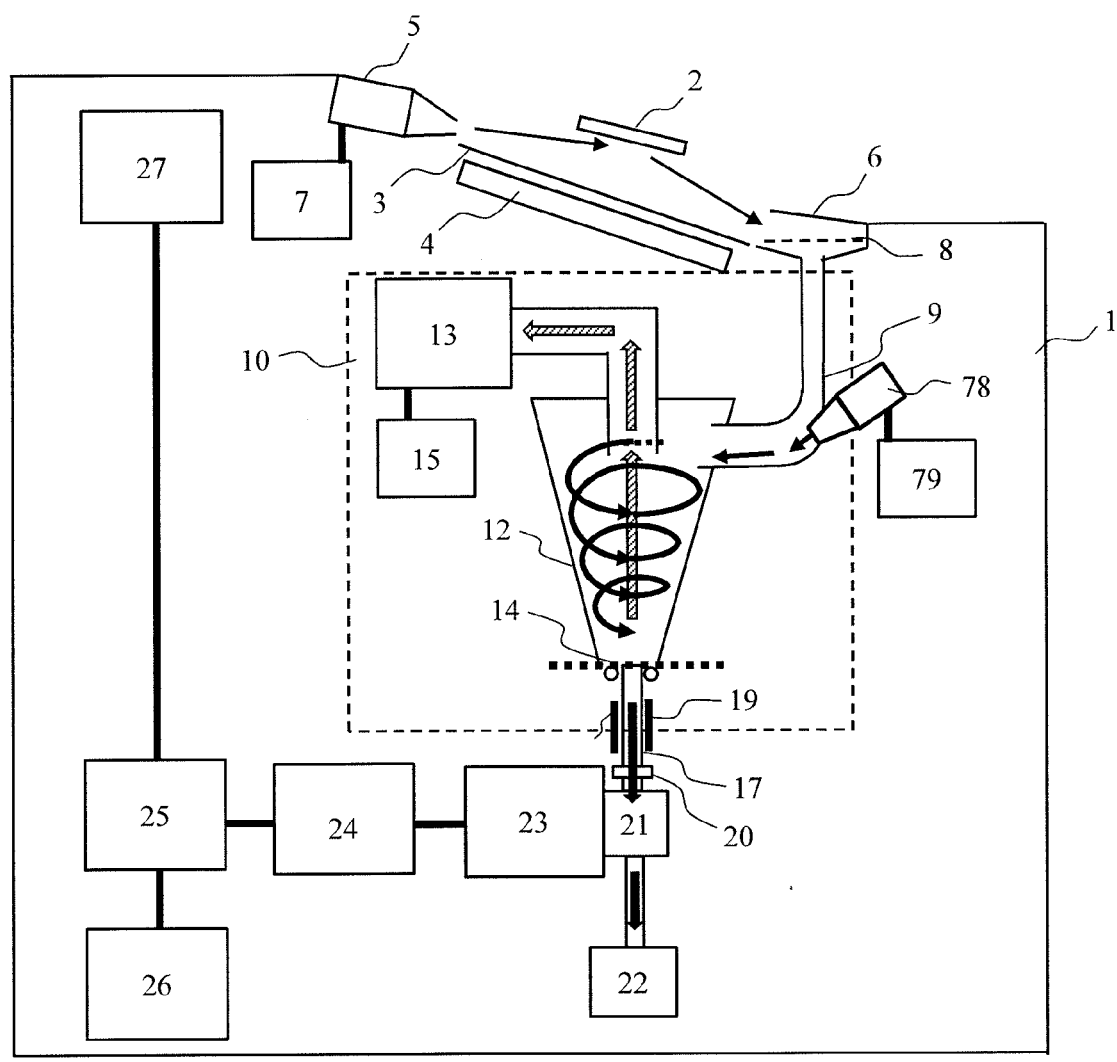
FIG. 32 shows an exemplary internal configuration of an analyzer according to the present invention.

Referring now to FIG. 32, the following describes sixth embodiment of the present invention.

An analyzer 1 of the present embodiment includes: an assistance blowing region 78 provided along the path of an introduction pipe 9 so as to inject air flow to the inner face of the introduction pipe 9 directed to a condensation device 12; and an assistance blowing region control unit 79 to control the assistance blowing region 78. The assistance blowing region 78 of the present embodiment is provided so as to inject air flow to a part where the path of the introduction pipe 9 changes into the horizontal direction. The following describes an advantageous effect obtained from the assistance blowing region 78 and the assistance blowing region control unit 79 provided in the analyzer 1.

After detecting trinitrotoluene explosives from an authentication target 2 by the analyzer 1 of the first embodiment, the present inventors examined whether the trinitrotoluene explosives were sampled or not at the collection filter 14 by injecting air flow to the introduction region 6 while generating a cyclonic effect inside the condensation device 12. As a result of the examination, it was found that the trinitrotoluene explosives were sampled at the collection filter 14. The present inventors found from this result that, once trinitrotoluene explosives are collected, the trinitrotoluene explosives particles are left inside the introduction pipe 9.

Examination of the subsequence authentication target 2 in a state where explosive particles remain on the inner wall of the introduction pipe 9 may cause the explosive particles attached to the inner wall of the introduction pipe 9 to be removed and be sampled at the collection filter 14. In this case, although explosive particles do not attach to the authentication target 2, the identification region 25 will detect the explosives, which becomes a factor of erroneous detection. Thus, it was found that a self-cleaning function in the introduction pipe 9 is a necessary function for the analyzer 1.

As possible cleaning means for the inner wall of the introduction pipe 9, an inspector may exchange the introduction pipe 9. However, such means leads to the following concerns about the safety of the inspector, the necessity of lengthy exchange operation, break at the introduction region 6, the sampling region 10 and the like or contamination of the introduction region 6 and the sampling region 10 due to newly generated dust and the like when the introduction pipe 9 is removed, and so such means is not practical. Thus, the analyzer 1 requires a function of automatic cleaning of the inner wall of the introduction pipe 9.

The self-cleaning function has the following challenges, including (1) duration required for self-cleaning is to be minimized for speedy resumption of examination; and (2) the cleaning effect has to be checked quantitatively in order to prevent erroneous detection.

The analyzer 1 of the present embodiment enables not manual but automatic cleaning of the introduction pipe 9, and enables quantitative examination of the cleaning effect as well.

Figure 33:
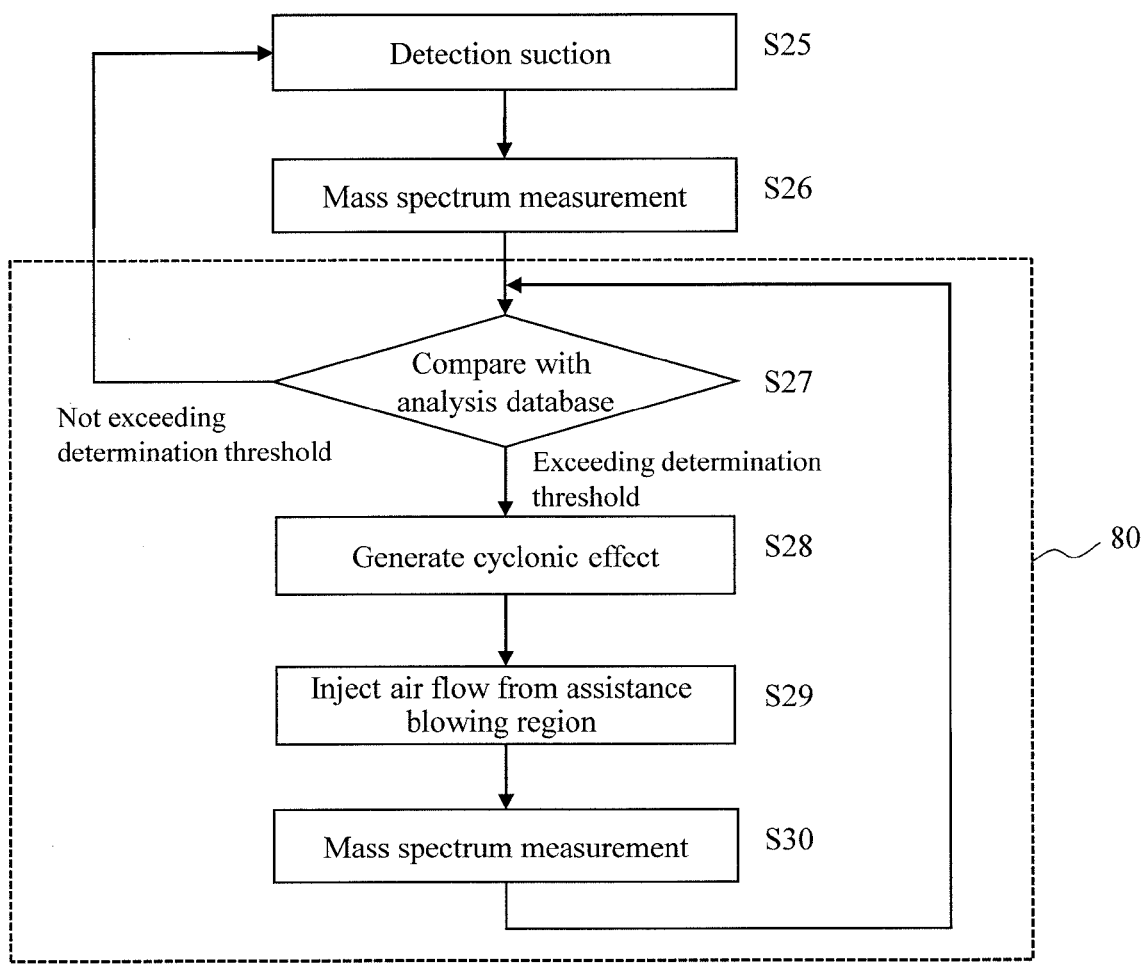
FIG. 33 shows exemplary self-cleaning procedure.

The self-cleaning by the analyzer 1 of the present embodiment is performed as follows. Referring to FIG. 33, the procedure is described below. In accordance with the detection procedure to detect a detection target substance described in the first embodiment, sample particles removed from the authentication target 2 are detected and sucked (S25), a mass spectrum of the sample particles is measured (S26) and signal intensity of the mass spectrum of the sample particles is compared with a determination threshold at the identification region 25 (S27). When the identification region 25 determines that the signal intensity of the mass spectrum of the sample particles exceeds the determination threshold, the monitor 27 displays as such for notification to the inspector. Thereafter, the analyzer 1 becomes a state to wait for an instruction to start self-cleaning process 80. When the inspector selects an execution instruction of the self-cleaning process 80, normal examination procedure stops, and the predetermined self-cleaning process 80 starts. The self-cleaning process 80 is performed in the procedure shown in FIG. 33.

A large intake pump is driven, and a cyclonic effect is generated inside a condensation device 12 (S28). Then, air flow is injected from an assistance blowing region 78 to the inside of an introduction pipe 9 (S29). In the present embodiment, air flow is injected for 0.5 sec. and at the injection pressure of 0.4 MPa. In accordance with the detection procedure described above, the sample particles remaining in the introduction pipe 9 and the sampling region 10 are removed by the air flow from the assistance blowing region 78, and a mass spectrum thereof is measured (S30), which is then compared with a determination threshold at the identification region 25. As a result of the comparison, the identification region 25 determines as the absence of explosives, and then normal determination process is resumed. On the other hand, when the identification region 25 determines as the presence of explosives, the self-cleaning process 80 starts again.

Figure 34:
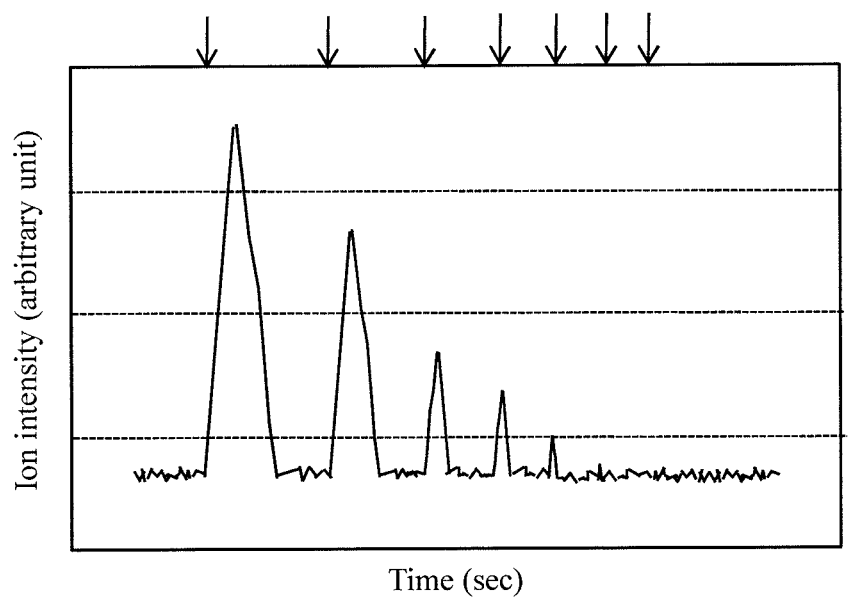
FIG. 34 schematically shows an exemplary mass spectrum of trinitrotoluene that is measured at the self-cleaning procedure.

FIG. 34 schematically shows exemplary mass spectrum signal intensity during the self-cleaning process 80, assuming the peak of m/z=227 of trinitrotoluene as a detection target. Arrows in this drawing indicate timing when air flow is injected from the assistance blowing region 78. The air flow injection interval is not regular from the assistance blowing region 78 because injection is performed manually. After detecting a trinitrotoluene component from the sample particles, the self-cleaning process 80 is executed, whereby air flow injected from the assistance blowing region 78 to the inside of the introduction pipe 9 removes sample particles remaining in the introduction pipe 9 and the sampling region 10, meaning that a mass spectrum derived from trinitrotoluene is obtained from the sample particles at the mass analysis region 23. Then, the self-cleaning process 80 is performed repeatedly until the signal intensity of the mass spectrum derived from trinitrotoluene becomes enough smaller than the determination threshold at the mass analysis region 23.

In the present embodiment, when the self-cleaning process 80 is repeated 7 times, then there is no signal found, derived from trinitrotoluene from the sample particles sampled at the sampling region 10. In this way, according to the present embodiment, letting that the air flow injection period from the assistance blowing region 78 is 1 sec., the self-cleaning can be completed in 7 sec.

The self-cleaning of the present embodiment enables automatic and short-time cleaning of the inside of the introduction pipe 9 after detection of explosive components from the authentication target 2 without contamination by a person and without break of components such as the introduction region 6 and the sampling region 10. Then, the cleanliness of the introduction pipe 9 after cleaning can be determined at the identification region 25, whereby the cleaning effect can be checked quantitatively, and so erroneous detection can be prevented after the examination following detection of explosive components. Herein, the effect of self-cleaning does not have to be checked after every self-cleaning. The effect of self-cleaning may be checked after the completion of self-cleaning performed a predetermined number of times, whereby duration required for the self-cleaning can be made shorter.

In synchronization with injection timing of air flow from the blowing region 5, air flow is injected from the assistance blowing region 78, whereby sample particles removed from the authentication target 2 can be conveyed to the collection filter 14 effectively.

Figure 35:
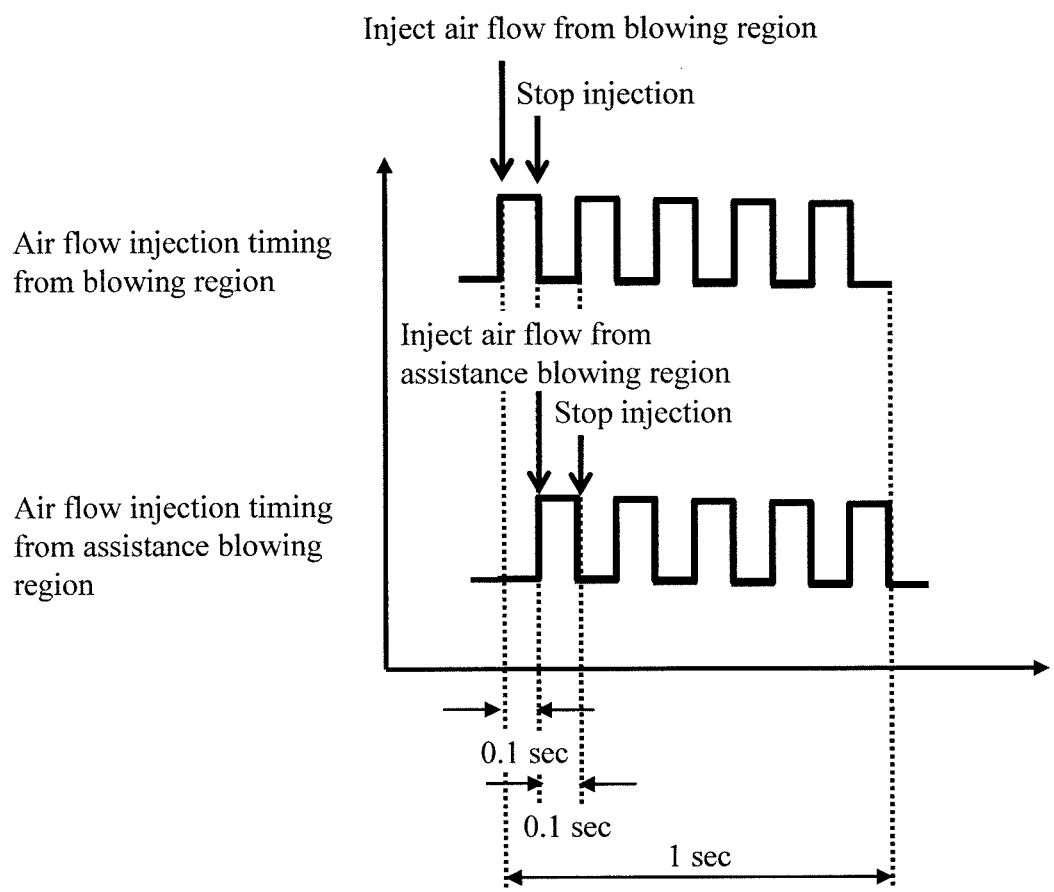
FIG. 35 shows exemplary operation timing of auxiliary air flow according to the present invention.

FIG. 35 is a time-sequence diagram showing exemplary timing to inject air flow from the blowing region 5 and the assistance blowing region 78 in normal examination in accordance with the above-described detection procedure.

The present inventors found from an experimental result that sample particles can be removed from the authentication target 2 by applying pulse-like air flow to the authentication target 2 a plurality of times. In the present embodiment, air flow is injected from the blowing region 5 and the assistance blowing region 78 for 0.1 sec., and then the air flow is stopped for 0.1 sec., which are repeated 5 times. The injection pressure of the air flow is 0.05 MPa. Air flow injected from the blowing region 5 and the assistance blowing region 78 at continuous timing can prevent sample particles removed from the authentication target 2 from remaining in the introduction pipe 9 and can convey the sample particles to the condensation device 12 effectively. Thus, the present embodiment enables detection of a very small amount of explosive particles attached to the authentication target 2, which could not be detected by the analyzer 1 without the assistance blowing region 78. In this way, the analyzer 1 having high detection sensitivity and less erroneous detection can be realized.

Figure 36:
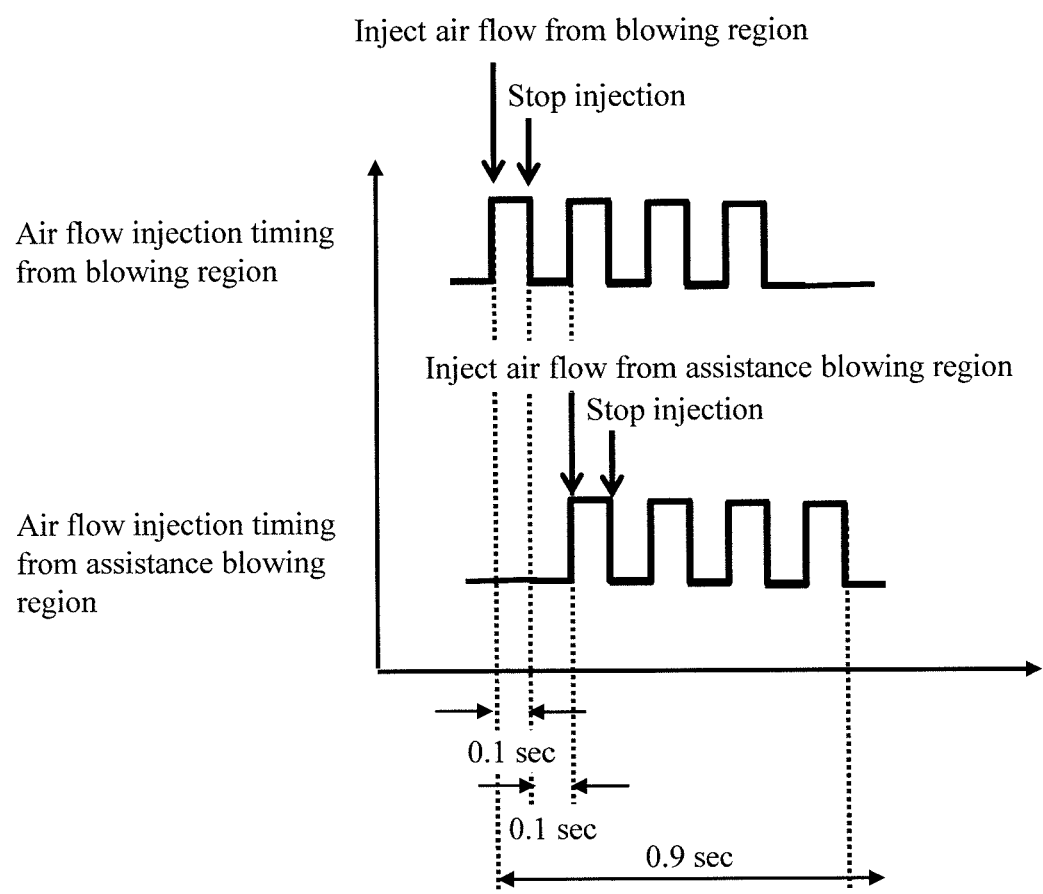
FIG. 36 shows another exemplary operation timing of auxiliary air flow according to the present invention.

In the present embodiment, after injection from the blowing region 5, air flow is injected from the assistance blowing region 78. Instead, as shown in FIG. 36, air flow may be injected simultaneously from the blowing region 5 and the assistance blowing region 78. In this case, as shown in FIG. 36, after the last air flow is injected from the blowing region 5, the last air flow is then injected from the assistance blowing region 78, whereby a similar effect to that of the examination at the injection timing of FIG. 35 can be obtained.

Figure 37:
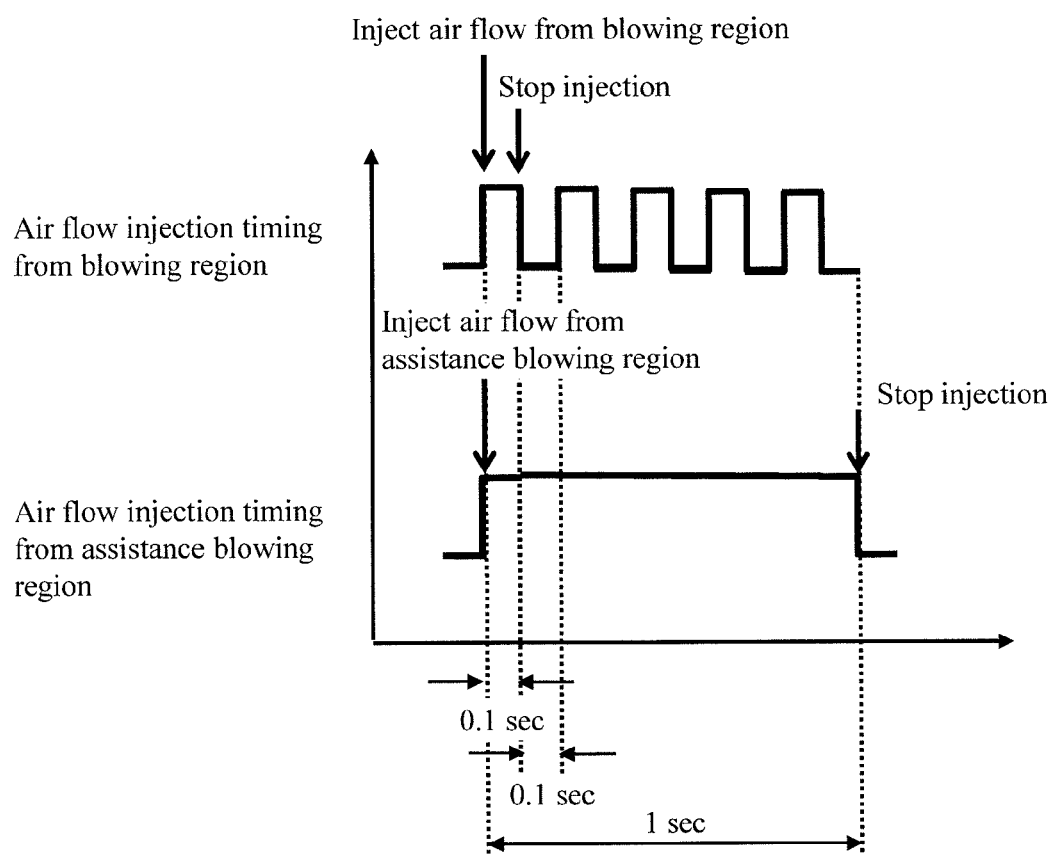
FIG. 37 shows still another exemplary operation timing of auxiliary air flow according to the present invention.

In the present embodiment, the injection duration of air flow from the assistance blowing region 78 is 0.1 sec, and air flow may be injected continuously. FIG. 37 is a time-sequence diagram showing exemplary timing to inject air flow from the blowing region 5 and the assistance blowing region 78 in normal examination in accordance with the above-described detection procedure. In the present embodiment, in synchronization with air flow injected from the blowing region 5, air flow is injected from the assistance blowing region 78 continuously. In this case, as shown in FIG. 37, after the last air flow is injected from the blowing region 5, the last air flow is then injected from the assistance blowing region 78, whereby a similar effect to that of the examination at the injection timing of FIG. 35 can be obtained. Although the air flow injection duration from the assistance blowing region 78 in the present embodiment is 1 sec, the air flow injection duration from the assistance blowing region 78 may be 1 sec. or longer, from which a similar effect can be obtained.

Alternatively, the assistance blowing region control unit 79 may control the assistance blowing region 78 so that, after normal examination process without the assistance blowing region 78, when the background for mass spectrum measurement becomes lower than the BG threshold, then air flow may be injected again from the assistance blowing region 78.

In general, during determination of the presence or not of an explosive component in the sample particles removed from the authentication target 2, signal intensity of the explosive component may be near the determination threshold to determine the presence or not of the explosive component. In such a case, determination is difficult, which may be a factor of erroneous detection. The present embodiment provided with the assistance blowing region 78 sends air flow to the inside of the introduction pipe 9 from the assistance blowing region 78 after normal examination where air flow is not injected from the assistance blowing region. Thereby the same sample particles removed from the authentication target 2 can be examined twice, including examination of the one remaining in the introduction pipe 9. Then, when signal intensity of the explosive component near the determination threshold is obtained twice in the examination performed twice, it may be determined as the presence of the explosive component, whereby erroneous detection can be reduced.

Although the thus described sixth embodiment is provided with the assistance blowing region 78 at the introduction pipe 9 only, a plurality of assistance blowing regions 78 may be provided so as to inject air flow to the inside of the introduction pipe 9 and the introduction region 6, from which a similar effect to that of the present embodiment can be obtained.

The present invention is not limited to the above-described embodiments, and may include various modification examples. For instance, the entire detailed configuration of the embodiments described above for explanatory convenience is not always necessary for the present invention. A part of one embodiment may be replaced with the configuration of another embodiment, or the configuration of one embodiment may be added to the configuration of another embodiment. The configuration of each embodiment may additionally include another configuration, or a part of the configuration may be deleted or replaced.

REFERENCE SIGNS LIST

1 Analyzer
2 Authentication Target
3 Authentication Plane
4 Authentication Region
5 Blowing Region
6 Introduction Region
7 Blowing Control Unit
8 Rough Mesh Filter
9 Introduction Pipe
10 Sampling region
11 Pipe Heater
12 Condensation Device
13 Large Intake Pump
14 Collection Filter
15 Collection Filter Control Unit
16 Anti Adsorption
17 Analysis Pipe
18 Collection Filter Heater
19 Analysis Pipe Heater
20 Fine Mesh Filter
21 Ion Source
22 Intake Pump
23 Mass Analysis Region
24 Data Processor
25 Identification Region
26 Mass Database Region
27 Monitor
28 Needle Electrode
29 Counter Electrode
30a First Aperture
30b Second Aperture
30c Third Aperture
31a First Differential Pumping Region
31b Second Differential Pumping Region
31c Vacuum Region
32a Vacuum Pump
32b Vacuum Pump
33 Ion Guide
34 Ion Trap Region
35a Inlet End Lens
35b Outlet End Lens
36 Quadruple Rods
37 Excitation Electrode
38a Trap Wire Electrode
38b Extraction Wire Electrode
39 Trap Region
40 Detector
41 Gas Supply Unit
50 Automatic Ticket Gate
51 Large Rotation Condensation Device
52 Small Rotation Condensation Device
53 Large Rotation Condensation Device
54a First Small Rotation Condensation Device
54b Second Small Rotation Condensation Device
55 Condensation Introduction Region
56 Small Rotation Condensation Device
57 Rough Mesh Filter
58 Gas Sampling Region
59 Particle Sampling Region
60 Fine Mesh Filter
61 Gas Introduction Pipe
62 Gas Introduction Pipe Heater
70 Gate
71 Subject
72 Grating
73 Bottom Introduction Region
74 Opposite Side Gate
75 Mesh
76 Side Introduction Region
77 Bottom Blowing Region
78 Assistance Blowing Region
79 Assistance Blowing Region Control Unit
80 Self-Cleaning Process
105a Cleaning Blowing Region
105b Cleaning Blowing Region
106 Sampling Cover
110 Blowing Cover
111 Introduction Cover

The invention claimed is:

1. An analyzer, comprising:
a blowing region configured to remove a sample attached to a target;
an introduction region configured to suck the sample removed from the target;
a sampling region having a conic condensation device, the sampling region being configured to condense and sample the sucked sample;
a large intake unit provided above the condensation device;
a collection filter provided at a small-radius part of the condensation device;

a heating unit that heats the collection filter provided at the small-radius part of the condensation device;
a small intake unit configured to continuously suck a sample from a rear face of the collection filter, the sample having been sampled to the collection filter and vaporized through the heating;
an ion source configured to introduce the sucked sample for ionization;
a mass analysis region configured to perform mass analysis of ions generated at the ion source;
a data processor configured to control the ion source and the mass analysis region;
a database unit configured to hold mass spectrum data derived from a detection target substance; and
an identification region configured to compare a result of mass analysis of the sample at the mass analysis region with the mass spectrum data held at the data base unit, thus determining presence or not of the detection target substance.

2. The analyzer according to claim 1, further comprising a conic first condensation device and a second condensation device at the sampling region, the first condensation device having a rotating radius larger than a rotating radius of the second condensation device, and the second condensation device being connected in series with the first condensation device on a downstream side of the first condensation device.

3. The analyzer according to claim 2, further comprising a plurality of the second condensation devices.

4. The analyzer according to claim 1, wherein the database unit holds a background threshold, and when background of the collection filter detected at the mass analysis region exceeds the background threshold held at the database unit, the collection filter is moved so as to expose a clean face of the collection filter.

5. The analyzer according to claim 1, wherein the introduction region includes a cover.

6. The analyzer according to claim 1, further comprising:
an introduction pipe coupling the introduction region with the condensation device;
an assistance blowing region configured to send pulse-like air flow having injection duration of 1 sec. or shorter to inside of the introduction pipe directed to the condensation device along a path of the introduction pipe; and
an assistance blowing region control unit configured to control the assistance blowing region.

7. The analyzer according to claim 1, further comprising:
an introduction pipe coupling the introduction region with the condensation device;
an assistance blowing region configured to send continuous air flow having injection duration of 1 sec. or longer to inside of the introduction pipe directed to the condensation device along a path of the introduction pipe; and
an assistance blowing region control unit configured to control the assistance blowing region.

8. The analyzer according to claim 6, wherein
the assistance blowing region control unit controls the assistance blowing region to send air flow in synchronization with injection timing of air flow injected from the blowing region.

9. The analyzer according to claim 6, wherein
the assistance blowing region sends the air flow to a part where the path of the introduction pipe changes into a horizontal direction.

10. An analyzer, comprising:
an authentication region including a face, to which an authentication target is to be brought closer;
an authentication database configured to hold authentication data;
a blowing region configured to send air flow along the authentication region, thus removing a sample attached to the authentication target;
an introduction region configured to suck the sample removed from the authentication target;
a sampling region having a conic condensation device, the sampling region being configured to condense and sample the sucked sample;
a large intake unit provided above the condensation device;
collection filter provided at a smell-radius part of the condensation device;
a heating unit that heats the collection filter provided at the small-radius part of the condensation device;
a small intake unit configured to continuously suck a sample from a rear face of the collection filter, the sample having been sampled to the collection filter and vaporized through the heating;
an ion source configured to introduce the sucked sample for ionization;
a mass analysis region configured to perform mass analysis of ions generated at the ion source;
a data processor configured to control the ion source and the mass analysis region;
a database unit configured to hold mass spectrum data derived from a detection target substance; and
an identification region configured to perform identification using both a determination result of presence or not of the detection target substance obtained by comparing a result of mass analysis of the sample at the mass analysis region with the mass spectrum data held at the data base unit, and a determination result of whether or not data on the authentication tar obtained in the authentication region agrees with the authentication data held in the authentication database.

11. The analyzer according to claim 10, further comprising a conic first condensation device and a second condensation device at the sampling region, the first condensation device having a rotating radius larger than a rotating radius of the second condensation device, and the second condensation device being connected in series with the first condensation device on a downstream side of the first condensation device.

12. The analyzer according to claim 11, further comprising a plurality of the second condensation devices.

13. The analyzer according to claim 10, wherein the database unit holds a background threshold, and when background of the collection filter detected at the mass analysis region exceeds the background threshold held at the database unit, the collection filter is moved so as to expose a clean face of the collection filter.

14. The analyzer according to claim 10, further comprising at the introduction region: a gas sampling region, a gas introduction pipe connecting the gas sampling region with the ion source, an introduction region for particles and an introduction pipe connecting the introduction region for particles with the sampling region.

15. The analyzer according to claim 10, wherein the authentication region includes a hole, and the analyzer further comprises a second blowing region that sends air flow to the authentication target via the hole.

16. The analyzer according to claim 10, further comprising a cleaning blowing region configured to inject air flow to the authentication region so as to remove a sample attached to the authentication region.

17. The analyzer according to claim 10, wherein the heating unit is operated at a temperature of 180° C. to 300° C.

18. An analyzer, comprising:
a gate letting a subject pass therethrough;
an identification region configured to detect approaching of the subject to the gate;
a blowing region provided at the gate, the blowing region being configured to send air flow to the subject passing through the gate, thus removing a sample attached to the subject;
an introduction region provided at a floor face or a side face of the gate, the introduction region being configured to suck the sample removed by the air flow sent by the blowing region;
a sampling region having a conic condensation device, the sampling region being configured to condense and sample the sucked sample;
a large intake unit provided above the condensation device;
a collection filter provided at a small-radius part of the condensation device;
a heating unit that heats the collection filter provided at the small-radius part of the condensation device;
a small intake unit con ed to continuous suck a sample from a rear face of the collection filter, the sample having been sampled to the collection filter and vaporized through the heating;
an ion source configured to introduce the sucked sample for ionization;
a mass analysis region configured to perform mass analysis of ions generated at the ion source;
a data processor configured to control the ion source and the mass analysis region;
a database unit configured to hold mass spectrum data derived from a detection target substance; and
an identification region configured to compare a result of mass analysis of the sample at the mass analysis region with the mass spectrum data held at the data base unit, thus determining presence or not of the detection target substance.

19. The analyzer according to claim 18, wherein the gate includes a first gate and a second gate provided at a position opposed to the first gate, the blowing region is built in the first gate, the introduction region is built in the second gate, and a laminar flow is formed from the blowing region to the introduction region.

20. An analysis method, comprising:
a step of acquiring authentication data from an approaching authentication target;
a first comparison step of comparing the acquired authentication data with authentication data held in an authentication database;
a step of removing a sample attached to the authentication target;
a step of sucking the removed sample;
a step of condensing and sampling the sucked sample to a surface of a heated collection filter by a principle of a cyclone;
step of continuously sucking a sample vaporized through heating from a rear face of the collection filter, and ionizing the sample;
a step of performing mass analysis of the ionized ions;
a second comparison step of comparing a mass spectrum obtained as a result of the mass analysis with mass spectrum data held at a database, the mass spectrum data being derived from a detection target substance; and
a step of performing identification using both a determination result of presence or not of a component substance of the detection target substance based on a result of the second comparison step, and a determination result of whether or not the acquired authentication data agrees with the authentication data held in the authentication database in the first comparison step.

* * * * *